United States Patent
Bansal

(10) Patent No.: US 10,105,416 B2
(45) Date of Patent: *Oct. 23, 2018

(54) METHODS OF TREATING MILD BRAIN INJURY

(71) Applicant: The Regents of the University of California, Oakland, CA (US)

(72) Inventor: Vishal Bansal, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/114,067

(22) PCT Filed: Feb. 5, 2015

(86) PCT No.: PCT/US2015/014692
§ 371 (c)(1),
(2) Date: Jul. 25, 2016

(87) PCT Pub. No.: WO2015/120203
PCT Pub. Date: Aug. 13, 2015

(65) Prior Publication Data
US 2016/0367637 A1    Dec. 22, 2016

Related U.S. Application Data

(63) Continuation-in-part of application No. 14/486,636, filed on Sep. 15, 2014, now Pat. No. 9,119,832.

(60) Provisional application No. 61/936,143, filed on Feb. 5, 2014.

(51) Int. Cl.
*A61K 38/22* (2006.01)
*A61K 38/08* (2006.01)
*A61K 38/16* (2006.01)
*A61K 38/18* (2006.01)

(52) U.S. Cl.
CPC .............. *A61K 38/22* (2013.01); *A61K 38/08* (2013.01); *A61K 38/16* (2013.01); *A61K 38/18* (2013.01)

(58) Field of Classification Search
CPC ................................ A61K 38/18; A61K 38/22
See application file for complete search history.

(56) References Cited

U.S. PATENT DOCUMENTS

| | | |
|---|---|---|
| 3,846,402 A | 11/1974 | Eckstein et al. |
| 4,223,019 A | 9/1980 | Momany |
| 4,223,020 A | 9/1980 | Momany |
| 4,223,021 A | 9/1980 | Momany |
| 4,224,316 A | 9/1980 | Momany |
| 4,226,857 A | 10/1980 | Momany |
| 4,228,155 A | 10/1980 | Momany |
| 4,228,156 A | 10/1980 | Momany |
| 4,228,157 A | 10/1980 | Momany |
| 4,228,158 A | 10/1980 | Momany |
| 4,410,512 A | 10/1983 | Bowers |
| 4,410,513 A | 10/1983 | Momany |
| 4,411,890 A | 10/1983 | Momany |
| 4,485,101 A | 11/1984 | Coy et al. |
| 4,650,787 A | 3/1987 | Schally et al. |
| 4,851,408 A | 7/1989 | Brantl |
| 4,880,777 A | 11/1989 | Momany |
| 5,030,630 A | 7/1991 | Brantl |
| 5,082,767 A | 1/1992 | Hatfield et al. |
| 5,206,235 A | 4/1993 | Fisher et al. |
| 5,283,241 A | 2/1994 | Bochis et al. |
| 5,284,841 A | 2/1994 | Chu et al. |
| 5,304,489 A | 4/1994 | Rosen |
| 5,310,737 A | 5/1994 | Fisher et al. |
| 5,317,017 A | 5/1994 | Ok et al. |
| 5,374,721 A | 12/1994 | Schoen et al. |
| 5,416,073 A | 5/1995 | Coy et al. |
| 5,430,144 A | 7/1995 | Schoen et al. |
| 5,434,261 A | 7/1995 | Schoen et al. |
| 5,486,505 A | 1/1996 | Bowers et al. |
| 5,492,916 A | 2/1996 | Morriello et al. |
| 5,492,920 A | 2/1996 | Chen et al. |
| 5,494,919 A | 2/1996 | Morriello et al. |
| 5,506,107 A | 4/1996 | Cunningham et al. |
| 5,534,494 A | 7/1996 | Bowers et al. |
| 5,536,716 A | 7/1996 | Chen et al. |
| 5,545,735 A | 8/1996 | Bochis et al. |
| 5,559,128 A | 9/1996 | Chakravarty et al. |
| 5,576,301 A | 11/1996 | Hymer et al. |
| 5,578,593 A | 11/1996 | Chen et al. |
| 5,579,301 A | 11/1996 | Ganson et al. |
| 5,583,130 A | 12/1996 | Bochis et al. |
| 5,635,379 A | 6/1997 | Deghenghi |
| 5,646,301 A | 7/1997 | Deghenghi |
| 5,652,235 A | 7/1997 | Chen et al. |
| 5,656,606 A | 8/1997 | Nargund et al. |
| 5,663,146 A | 9/1997 | Bowers et al. |
| 5,663,171 A | 9/1997 | Chen et al. |
| 5,668,254 A | 9/1997 | Deghenghi |
| 5,672,596 A | 9/1997 | Wyvratt et al. |
| 5,691,377 A | 11/1997 | Estienne et al. |

(Continued)

FOREIGN PATENT DOCUMENTS

| | | |
|---|---|---|
| EP | 1186293 | 3/2002 |
| EP | 1258250 | 11/2002 |

(Continued)

OTHER PUBLICATIONS

Habedanck, Robert, International Search Report and Written Opinion, PCT/US2015/014692, European Patent Office, dated Jul. 1, 2015.

(Continued)

*Primary Examiner* — Robert C Hayes
(74) *Attorney, Agent, or Firm* — Joseph R. Baker, Jr.; Gavrilovich, Dodd & Lindsey LLP

(57) ABSTRACT

The present disclosure provides methods for treating mild brain injury and other neurological disorders in a subject, comprising administering to the subject an effective amount of a compound comprising ghrelin.

25 Claims, 3 Drawing Sheets
Specification includes a Sequence Listing.

(56) References Cited

U.S. PATENT DOCUMENTS

| | | |
|---|---|---|
| 5,721,250 A | 2/1998 | Morriello et al. |
| 5,721,251 A | 2/1998 | Chen et al. |
| 5,726,307 A | 3/1998 | Schoen et al. |
| 5,726,319 A | 3/1998 | Lin et al. |
| 5,731,317 A | 3/1998 | Lu et al. |
| 5,763,447 A | 6/1998 | Jacobus et al. |
| 5,767,085 A | 6/1998 | Johansen et al. |
| 5,767,118 A | 6/1998 | Nargund et al. |
| 5,767,124 A | 6/1998 | Draper et al. |
| 5,773,441 A | 6/1998 | Hipskind et al. |
| 5,773,448 A | 6/1998 | Gallagher et al. |
| 5,776,901 A | 7/1998 | Bowers et al. |
| 5,777,112 A | 7/1998 | Nargund et al. |
| 5,783,582 A | 7/1998 | Guo et al. |
| 5,798,337 A | 8/1998 | Somers et al. |
| 5,804,578 A | 9/1998 | Chakravarty et al. |
| 5,807,985 A | 9/1998 | Deghenghi |
| 5,817,654 A | 10/1998 | Thogersen et al. |
| 5,830,433 A | 11/1998 | Dean et al. |
| 5,837,861 A | 11/1998 | Pendergast et al. |
| 5,854,211 A | 12/1998 | Johansen et al. |
| 5,872,100 A | 2/1999 | Deghenghi |
| 5,877,182 A | 3/1999 | Nargund et al. |
| 5,936,089 A | 8/1999 | Carpino et al. |
| 6,468,974 B1 | 10/2002 | Bowers et al. |
| 6,849,597 B2 | 2/2005 | Murata et al. |
| 6,967,237 B2 | 11/2005 | Bednarek |
| 7,452,862 B2 | 11/2008 | Deslongchamps et al. |
| 7,456,253 B2 | 11/2008 | Dong |
| 7,476,653 B2 | 1/2009 | Hoveyda et al. |
| 7,491,695 B2 | 2/2009 | Fraser et al. |
| 7,521,420 B2 | 4/2009 | Fraser et al. |
| 7,550,431 B2 | 6/2009 | Deslongchamps et al. |
| 7,589,058 B2 | 9/2009 | Dong et al. |
| 7,763,707 B2 | 7/2010 | Mintz |
| 7,829,589 B2 | 11/2010 | Saunders et al. |
| 7,923,442 B2 | 4/2011 | Kuzma et al. |
| 7,937,145 B2 | 5/2011 | Dobak |
| 7,981,860 B2 | 7/2011 | Mintz |
| 8,088,733 B2 | 1/2012 | Fraser et al. |
| 8,192,719 B2 | 6/2012 | Larsen |
| 8,324,151 B2 | 12/2012 | Wang |
| 8,377,865 B2 | 2/2013 | Dong |
| 8,492,368 B2 | 7/2013 | Vanlandingham et al. |
| 8,518,893 B2 | 8/2013 | Minamitake et al. |
| 8,618,074 B2 | 12/2013 | Lechleiter |
| 8,673,860 B2 | 3/2014 | Schellenberger et al. |
| 8,791,149 B2 | 7/2014 | McKnight et al. |
| 9,119,832 B2 | 9/2015 | Bansal |
| 2002/0094992 A1 | 7/2002 | MacLean et al. |
| 2003/0027755 A1 | 2/2003 | Guan et al. |
| 2003/0105114 A1 | 6/2003 | Carpino et al. |
| 2003/0186865 A1 | 10/2003 | Acosta et al. |
| 2004/0081652 A1 | 4/2004 | Zack et al. |
| 2006/0025566 A1 | 2/2006 | Hoveyda et al. |
| 2006/0058222 A1 | 3/2006 | Miller |
| 2007/0238662 A1 | 10/2007 | Mintz |
| 2008/0033511 A1 | 2/2008 | Dobak |
| 2008/0207679 A1 | 8/2008 | Berkowitz |
| 2010/0143310 A1 | 6/2010 | Murakami et al. |
| 2010/0216706 A1 | 8/2010 | Horvath et al. |
| 2010/0233159 A1 | 9/2010 | Relton et al. |
| 2010/0267812 A1 | 10/2010 | Dodge et al. |
| 2011/0015217 A1 | 1/2011 | McKnight et al. |
| 2011/0160133 A1 | 6/2011 | Dong et al. |
| 2011/0237664 A1 | 9/2011 | Dalton et al. |
| 2012/0135918 A1 | 5/2012 | Bowers et al. |
| 2012/0232001 A1 | 9/2012 | Prestrelski et al. |
| 2012/0302526 A1 | 11/2012 | Barth et al. |
| 2013/0090315 A1 | 4/2013 | Vanlandingham et al. |
| 2013/0090317 A1 | 4/2013 | Vanlandingham et al. |
| 2013/0090458 A1 | 4/2013 | Govindan et al. |
| 2013/0178823 A1 | 7/2013 | Buchine et al. |
| 2014/0018299 A1 | 1/2014 | Mondello et al. |
| 2014/0024053 A1 | 1/2014 | Kobeissy et al. |
| 2014/0094480 A1 | 4/2014 | McKnight et al. |
| 2014/0161807 A1 | 6/2014 | Gonias et al. |
| 2014/0255517 A1 | 9/2014 | Ressler |
| 2015/0037349 A1 | 2/2015 | Castanheira Aires da Silva et al. |
| 2015/0136130 A1 | 5/2015 | Dehaan et al. |
| 2015/0216939 A1 | 8/2015 | Bansal |
| 2017/0281732 A1 | 10/2017 | Shah |

FOREIGN PATENT DOCUMENTS

| | | |
|---|---|---|
| EP | 1312363 | 5/2003 |
| EP | 1 529 533 A1 | 5/2005 |
| EP | 1354597 | 8/2005 |
| EP | 1 994 939 A1 | 11/2008 |
| EP | 2052738 | 4/2009 |
| EP | 2489733 | 8/2012 |
| EP | 2733149 | 5/2014 |
| WO | 83/02272 | 7/1983 |
| WO | 89/07110 | 8/1989 |
| WO | 89/07111 | 8/1989 |
| WO | 89/10933 | 11/1989 |
| WO | 92/01711 | 2/1992 |
| WO | 92/16524 | 10/1992 |
| WO | 93/04081 | 3/1993 |
| WO | 94/05634 | 3/1994 |
| WO | 94/07483 | 4/1994 |
| WO | 94/07486 | 4/1994 |
| WO | 94/07519 | 4/1994 |
| WO | 94/08583 | 4/1994 |
| WO | 94/11012 | 5/1994 |
| WO | 94/11397 | 5/1994 |
| WO | 94/13696 | 6/1994 |
| WO | 94/18169 | 8/1994 |
| WO | 94/19367 | 9/1994 |
| WO | 95/03289 | 2/1995 |
| WO | 95/03290 | 2/1995 |
| WO | 95/09633 | 4/1995 |
| WO | 95/12598 | 5/1995 |
| WO | 95/13069 | 5/1995 |
| WO | 95/14666 | 6/1995 |
| WO | 95/16675 | 6/1995 |
| WO | 95/16692 | 6/1995 |
| WO | 95/16707 | 6/1995 |
| WO | 95/17422 | 6/1995 |
| WO | 95/17423 | 6/1995 |
| WO | 95/34311 | 12/1995 |
| WO | 96/02530 | 2/1996 |
| WO | 96/05195 | 2/1996 |
| WO | 96/10040 | 4/1996 |
| WO | 96/13265 | 5/1996 |
| WO | 96/15148 | 5/1996 |
| WO | 96/22782 | 8/1996 |
| WO | 96/22997 | 8/1996 |
| WO | 96/24580 | 8/1996 |
| WO | 96/24587 | 8/1996 |
| WO | 96/32126 | 10/1996 |
| WO | 96/32943 | 10/1996 |
| WO | 96/33189 | 10/1996 |
| WO | 96/35713 | 11/1996 |
| WO | 96/38471 | 12/1996 |
| WO | 97/00894 | 1/1997 |
| WO | 97/11697 | 4/1997 |
| WO | 97/15191 | 5/1997 |
| WO | 97/15573 | 5/1997 |
| WO | 97/15574 | 5/1997 |
| WO | 97/18233 | 5/1997 |
| WO | 97/21730 | 6/1997 |
| WO | 97/22367 | 6/1997 |
| WO | 97/22620 | 6/1997 |
| WO | 97/22622 | 6/1997 |
| WO | 97/23508 | 7/1997 |
| WO | 97/24369 | 7/1997 |
| WO | 97/25057 | 7/1997 |
| WO | 97/27298 | 7/1997 |
| WO | 97/34604 | 9/1997 |
| WO | 97/39768 | 10/1997 |
| WO | 97/40023 | 10/1997 |
| WO | 97/40071 | 10/1997 |

(56) References Cited

FOREIGN PATENT DOCUMENTS

| WO | 97/42223 | 11/1997 |
|---|---|---|
| WO | 98/03473 | 1/1998 |
| WO | 98/10653 | 3/1998 |
| WO | 98/16527 | 4/1998 |
| WO | 98/25622 | 6/1998 |
| WO | 98/25897 | 6/1998 |
| WO | 98/46220 | 10/1998 |
| WO | 98/46569 | 10/1998 |
| WO | 98/50036 | 11/1998 |
| WO | 98/51687 | 11/1998 |
| WO | 98/58947 | 12/1998 |
| WO | 98/58948 | 12/1998 |
| WO | 98/58949 | 12/1998 |
| WO | 98/58950 | 12/1998 |
| WO | 99/08699 | 2/1999 |
| WO | 99/09991 | 3/1999 |
| WO | 99/09998 | 3/1999 |
| WO | 00/48623 | 8/2000 |
| WO | 200208250 | 1/2002 |
| WO | 2003049761 | 6/2003 |
| WO | 2004007675 | 1/2004 |
| WO | 2004009616 | 1/2004 |
| WO | 2005/039625 A1 | 5/2005 |
| WO | 2005044295 | 5/2005 |
| WO | 2006/045314 A2 | 5/2006 |
| WO | 2006/079077 A2 | 7/2006 |
| WO | 2007146046 | 12/2007 |
| WO | 2007146287 | 12/2007 |
| WO | 2008143835 A1 | 11/2008 |
| WO | 2009020643 | 2/2009 |
| WO | 2009071283 | 6/2009 |
| WO | 2013004203 | 1/2013 |
| WO | 2013113916 | 8/2013 |
| WO | 2013119650 | 8/2013 |
| WO | 2013/130683 A2 | 9/2013 |
| WO | 2014/172341 A1 | 10/2014 |
| WO | 2015/017123 A1 | 2/2015 |
| WO | 2015/120203 A1 | 8/2015 |
| WO | 2016/028826 A1 | 2/2016 |
| WO | 2016/048488 A1 | 3/2016 |
| WO | 2016134215 | 8/2016 |

OTHER PUBLICATIONS

Hossienzadeh Fezzeh et al., "Effect of ghrelin on brain edema induced by acute and chronic systemic hypoxia", Neuroscience Letters, Limerick, IE, vol. 534, Jan. 4, 2013, pp. 47-51.
Lopez, N.E. et al., "Early ghrelin treatment attenuates disruption of the blood brain barrier and apoptosis after traumatic brain injury through a UCP-2 mechanism", Brain Research, vol. 1489, Dec. 1, 2012, pp. 140-148.
Lopez, Nicole E. et al., "Ghrelin decreases motor deficits after traumatic brain injury", Journal of Surgical Research, vol. 187, No. 1, Oct. 7, 2013, pp. 230-236.
Adelson, et al. Guidelines for the Management of Severe Traumatic Brain Injury. Journal of Neurotrauma, 2007, vol. 24, Supplement 1, S1-S106 (Exhibit 1).
Ahmadzadeh, et al. Viscoelasticity of tau proteins leads to strain rate-dependent breaking of microtubules during axonal stretch injury: predictions from a mathematical model. Biophys J. Mar. 4, 2014;106(5):1123-33 (Exhibit 2).
Albarrán-Zeckler R.G. et al. The ghrelin receptors (GHS-R1a and GHS-Rib) Endocr Dev. Basel, Kager, 2013, vol. 25, pp. 5-15 (Exhibit 14).
Andrews ZB, Erion Beiler R, et al. Ghrelin promotes and protects nigrostriatal dopamine function via a UCP2-lepemdent mitochondrial mechanism. The Journal of neuroscience: the official journal of the Society for Neuroscience. Nov. 11, 2009; 29(45):14057-14065 (Exhibit 5).
Andrews ZB, Erion OM, Beiler R, Choi CS, Shulman GI, Horvath TL. Uncoupling pFrotein-2 decreases the lipogenic actions of ghrelin. Endocrinology. May 2010; 151 (5):2078-2086 (Exhibit 6).

Andrews ZB, Liu ZW. Wallingford N, et al. UCP2 mediates ghrelin's action on NPY/AgRP neurons by lowering free radicals. Nature. Aug. 14, 2008;454(7206): 846-851 (Exhibit 7).
Andrews ZB. Central mechanisms involved in the orexigenic actions of ghrelin. Peptides. Nov. 2011; 32(11): 2248-2255 (Exhibit 3).
Andrews ZB. The extra-hypothalamic actions of ghrelin on neuronal function. Trends in neurosciences. Jan. 2011; 34(1): 31-40 (Exhibit 4).
Babri, et al. Effects of intrahippocampal injection of ghrelin on spatial memory in PTZ-induced seizures in male rats. Neuropeptides. Oct. 2013; 47(5):355-60 (Exhibit 10).
Bai, Lingfei, International Preliminary Report on Patentability, International Application No. PCT/US2016/018602, dated Aug. 22, 2017.
Bansal, Vishal et al., "Stimulating the Central Nervous System to Prevent Intestinal Dysfunction After Traumatic Brain Injury", The Journal of Trauma, vol. 68, No. 5, May 2010, pp. 1059-1064.
Bansal, Vishal et al., "The Hormone Ghrelin Prevents Traumatic Brain Injury Induced Intestinal Dysfunction," Journal of Neurotrauma, 27: 2255-2260 (Dec. 2010).
Bansal, Vishal et al., "Traumatic Brain Injury and Intestinal Dysfunction: Uncovering the Neuro-Enteric Axis," J Neurotrauma, Aug. 26, 2009(8), pp. 1353-1359.
Bansal, Vishal et al., "Vagal Stimulation Modulates Inflammation Through a Ghrelin Mediated Mechanism in Traumatic Brain Injury," Inflammation, vol. 35, No. 1, Feb. 2012, pp. 214-220.
Barkhoudarian et al., The Molecular Pathophysiology of Concussive Brain Injury, Clin Sports Med 30 (2011) 33-48—Exhibit 42.
Bayliss JA, Andrews ZB. Ghrelin is neuroprotective in Parkinson's disease: molecular mechanisms of metabolic neuroprotection. Therapeutic advances in endocrinology and metabolism. Feb. 2013;4(1):25-36 (Exhibit 11).
Beck, B. and Pourie, G. Ghrelin, neuropeptide Y, and other feeding-regulatory peptides active in the hippocampus: role in learning and memory. Nutr Rev. Aug. 2013;71(8):541-61 (Exhibit 8).
Bigler. Neuropsychology and clinical neuroscience of persistent post-concussive syndrome. J Int Neuropsychol Soc. Jan. 2008;14(1):1-22 (Exhibit 12).
Brand MD, Esteves TC. Physiological functions of the mitochondrial uncoupling proteins UCP2 and UCP3. Cell metabolism. Aug. 2005; 2(2):85-93 (Exhibit 9).
Carney, N., et al. Concussion guidelines step 1: systematic review of prevalent indicators. Neurosurgery. Sep. 2014;75 Suppl 1:S3-15 (Exhibit 13).
Chen, et al., "Measurement of oxidative burst in neutrophils," Methods Mol Biol., 844: 115-124 (2012).
Copenheaver, Blaine R., International Search Report and Written Opinion, International Application No. PCT/US16/18602, dated May 2, 2016.
Coppola A., et al. A central thermogenic-like mechanism in feeding regulation: an interplay between arcuate nucleus T3 and UCP2. Cell Metab. 2007; 5:21-33 (Exhibit 15).
Diano S, Farr SA Benoit SC, et al. Ghrelin controls hippocampal spine synapse density and memory performance. Nature neuroscience. Mar. 2006; 9(3):381-388 (Exhibit 16).
Dixon and Kline 2009 "Animal models of acute neurological injuries. Chapter 33: controlled cortical impact injury model" Edited by Chen; New York, Totowa, NJ. p. 385-391.
Eisenberg, Meehan et al., Duration and course of post-concussive symptoms. Pediatrics. Jun. 2014;133(6):999-1006 (Exhibit 17).
Ersahin M., et al. The Anti-Inflammatory and Neuroprotective Effects of Ghrelin in Subarachnoid Hemorrhage-Induced Oxidative Brain Damage in Rats. J. Neurotrauma. Jun. 2010; 27(6): 1143-55 (Exhibit 18).
Faul et al., Epidemiology of traumatic brain injury. Handbook Clin Neural. 2015;127:3-13 (Exhibit 19).
Gahete, M. et al. Ghrelin gene products, receptors, and GOAT enzyme: biological and pathophysiological insight. J Endocrinol. Dec. 2, 2013;220(1):R1-24 (Exhibit 20).
GenBank® Accession No. NP_057446 or Swiss-Prot Identifier GHRL_HUMAN.

(56) References Cited

OTHER PUBLICATIONS

Hassouna et al., "Actions of Agonists and Antagonists of the Ghrelin/GHS-R Pathway on GH Secretion, Appetite, and cFos Activity," Frontiers in Endocrinology, Mar. 18, 2013, vol. 4, pp. 25.

Katayama Y, et al., "Massive increases in extracellular potassium and the indiscriminate release of glutamate following concussive brain injury," J Neurosurg. Dec. 1990; 73(6):889-900.

Kenny R, Cai G, Bayliss JA, et al. Endogenous ghrelin's role in hippocampal neuroprotection after global cerebral schemia: does endogenous ghrelin protect against global stroke? American Journal of Physiology. Regulatory, ntegrative and comparative physiology. Jun. 1, 2013; 304(11):R980-990 (Exhibit 22).

Kojima and Kangawa., Ghrelin, and orexigenic signaling molecule from the gastrointestinal tract Current Opinion in Pharmacology 2002, 2:665-668 (Exhibit 25).

Kojima M1, Kangawa K., Ghrelin: structure and function. Physiol Rev. Apr. 2005;85(2):495-522 (Exhibit 24).

Kojima, et al., "Ghrelin is a growth-hormone-releasing acylated peptide from stomach," Nature, vol. 402, Dec. 1999, pp. 656-660.

Kontos, H. Superoxide production in experimental brain injury. J Neurosurg. May 1986;64(5):803-7 (Exhibit 26).

Krishnan BR, Blakesley RW, Berg DE. Linear amplification DNA sequencing directly from single phage plaques and bacterial colonies. Nucleic acids research. Mar. 11, 1991; 19(5):1153 (Exhibit 23).

Li et al. Ghrelin directly stimulates adult hippocampal neurogenesis: implications for learning and memory. Endocr J. 2013;60(6):781-9 (Exhibit 27).

Liu, Y. et al. Both ischemic preconditioning and ghrelin administration protect hippocampus from ischemia/reperfusion and upregulate uncoupling protein-2. BMC Physiol. Sep. 22, 2009;9:17 (Exhibit 28).

Lopez, Nicole E. et al., "Ghrelin Prevents Disruption of the Blood-Brain Barrier After Traumatic Brain Injury," J Neurotrauma. Jan. 20, 2012;29(2):385-393.

Mattiasson G, Shamloo M, Gido G, et al. Uncoupling protein-2 prevents neuronal death and diminishes brain dysfunction after stroke and brain trauma. Nature Medicine. Aug. 2003; 9(8):1062-1068 (Exhibit 29).

Merriam-Webster "Full definition of amorphous" accessed from www.merriam-webster.com on Nov. 18, 2014 (excerpt).

Moon et al., Ghrelin Ameliorates Cognitive Dysfunction and Neurodegeneration in Intrahippocampal Amyloid-1-42 Oligomer-Injected Mice Journal of Alzheimer's Disease 23 (2011) 147-159-Exhibit 41.

Moon, Kihwan, International Preliminary Report on Patentability, International Application No. PCT/US2015/014692; dated Aug. 9, 2016.

Patchett et al., "Design and Biological Activities of L-163,191 (MK-0677): A Potent, Orally Active Growth Hormone Secretagogue," Proc. Natl. Acad. Sci. USA, (1995) vol. 92, pp. 7001-7005.

[Poster] Lee et al. Ghrelin treatment alters neuronal leukocyte recruitment following traumatic brain injury (also known as Altering Neuronal Leukocyte Recruitment Following Traumatic Brain Injury With Ghrelin Therapy). UC San Diego—Health Science, Neurotrauma, 2013 (Exhibit 40).

Prins ML, Alexander D, Giza CC, Hovda DA. Repeated mild traumatic brain injury: mechanisms of cerebral vulnerability. Journal of Neurotrauma. Jan. 1, 2013; 30(1):30-38 (Exhibit 30).

Qi et al. Ghrelin attenuates brain injury after traumatic brain injury and uncontrolled hemorrhagic shock in rats. Mol Med. 2012; 18: 186-93 (Exhibit 32).

Reuben et al., Postconcussion syndrome (PCS) in the emergency department: predicting and pre-empting persistent symptoms following a mild traumatic brain injury, Emerg Med J. 2014; 31: 72-77-Exhibit 43.

Roth TL, Nayak D, Atanasijevic T, Koretsky AP, Latour LL, McGavern DB. Transcranial amelioration of inflammation and cell death after brain injury. Nature. Jan. 9, 2014; 505(7482):223-228 (Exhibit 33).

Saatman, K. et al. Classification of traumatic brain Injury for targeted therapies. J Neurotrauma. Jul. 2008;25(7):719-38 (Exhibit 34).

Santos, D. et al. Ghrelin as a neuroprotective and palliative agent in Alzheimer's and Parkinson's disease. Curr Pharm Des. 2013; 19(38):6773-90 (Exhibit 35).

Schultz et a. 2012 "Repeated mild lateral fluid percussion brain injury in the rat causes cumulative long-term behavioral impairments, neuroinflammation, and cortical loss in an animal model of repeated concussion" J Neurotrauma 29:281-294.

Shin et al., "Randomized Controlled Phase Ib Study of Ghrelin Agonist, RM-131, in Type 2 Diabetic Women With Delayed Gastric Emptying," Diabetes Care, (2013) vol. 36, pp. 41-48.

Signoretti, S., et al., The pathophysiology of concussion, PM R Oct. 2011;3(10 Suppl 2):S359-68.

Singh R, Meier TB, Kuplicki R, et al. Relationship of collegiate football experience and concussion with hippocampal volume and cognitive outcomes. Jama. May 14, 2014; 311 (18):1883-1888 (Exhibit 36).

Singh, I. et al. Time course of post-traumatic mitochondrial oxidative damage and dysfunction in a mouse model of focal traumatic brain injury: implications for neuroprotective therapy. J Cereb Blood Flow Metab. Nov. 2006;26 ;(11):1407-18 (Exhibit 37).

Tocris "Ghrelin (human)" accessed from www.tocris.com on Nov. 21, 2014 (excerpt).

Washington, et al. The effect of injury severity on behavior: A phenotypic study of cognitive and emotional deficits after mild, moderate, and severe controlled cortical impact injury in mice. J of Neurotrauma 2012, 29: 2283-2296 (Exhibit 38).

Wei, E.P. et al. Inhibition by free radical scavengers and by cyclooxygenase inhibitors of pial arteriolar abnormalities from concussive brain injury in cats. Circ Res. Jan. 1981;48(1):95-103 (Exhibit 39).

Ku et al., "Predictive Value of Early Decreased Plasma Ghrelin Level for Three-Month Cognitive Deterioration in Patients with Mild Traumatic Brain Injury," Peptides (2014), vol. 54.

Ali et al. "Clinical Development of Ghrelin Axis Derived Molecules for Cancer Cachexia," Curr Opin Support Palliat Care, Dec. 1, 2013, vol. 7, pp. 368-375.

Anonymous: "Updated mild traumatic brain injury guidelines for adults", CDC.gov.website, Mar. 5, 2018, URL: https://www.cdc.gov/traumaticbraininjury/pdf/tbi_clinicians_factsheet-a.pdf (2 pages).

Aoyama et al., "Duration of ATP reduction affects extent of CA1 cell death in rat models of fluid percussion injury combined with secondary ischemia", Brain Res., 2008, 1230:310-9.

Ariyasu et. al., "Delayed short-term secretory regulation of ghrelin in obese animals: evidenced by a specific RIA for the active form of ghrelin", Endocrinology, 2002, 143(9), 3341-3350.

Bai, Lingfei, PCT International Preliminary Report on Patentability (Chapter 1) for Application No. PCT/US2016/021404 dated Sep. 21, 2017. (13 pages).

Banati, R. B., et. al. (1991). Respiratory burst activity in brain macrophages: a flow cytometric study on cultured rat microglia. Neuropathology and applied neurobiology, 17(3), 223-230.

Becker, G. W. (2008). Stable isotopic labeling of proteins for quantitative proteomic applications. Briefings in functional genomics & proteomics, 7(5), 371-382.

Bednarek et al., "Structure—Function Studies on the New Growth Hormone-Releasing Peptide, Ghrelin: Minimal Sequence of Ghrelin Necessary for Activation of Growth Hormone Secretagogue Receptor 1a1", Journal of Medicinal Chemistry, 2000, 43(23), 4370-4376.

Berg, R. A., "Screening Tests in Clinical Neuropsychology", The Neuropsychology Handbook, 1997, vol. 1, Chapter 10, pp. 331-363.

Borg et al., "Serum Levels of Biochemical Markers of Traumatic Brain Injury", ISRN Emergency Medicine, 2012, 2012, 1-7.

Bramel, Jene, "Concussion Management in the NFL: The Return to Play Protocol", Oct. 3 Photo: Brace Hemmelgarn, US Presswire—http://subscribers.footballguys.com/apps/article.php?article=13bramel_inside_concussions_2.

Brigelius-Flohe, R., "Tissue-specific functions of individual glutathione peroxidases", Free Radical Biology and Medicine, 1999, 27(9/10), 951-965.

(56) References Cited

OTHER PUBLICATIONS

BTrackSTM System (http://balancetrackingsystems.com/); Balance Tracking Systems Inc., 2016. (11 pages).
Cantu et al., "Second-impact syndrome, A risk in any contact sport", Physician and Sports Medicine, 1995, 23(6): p. 27-34.
Cantu, R. C. (1998). Second-impact syndrome. Clinics in sports medicine, 17(1), 37-44.
Chambers et. al., "The structure of the mouse glutathione peroxidase gene: the selenocysteine in the active site is encoded by the'termination'codon, TGA", The EMBO journal, 1986, 5(6), 1221-1227.
Chen, Ying, et al. (2010). Ghrelin modulates insulin sensitivity and tau phosphorylation in high glucose-induced hippocampal neurons. Biological and Pharmaceutical Bulletin 33.7, pp:1165-1169.
Chu et al., "Expression of plasma glutathione peroxidase in human liver in addition to kidney, heart, lung, and breast in humans and rodents", Blood, 1992, 79(12), 3233-3238.
Chu et al., "Expression, characterization, and tissue distribution of a new cellular selenium-dependent glutathione peroxidase, GSHPx-GI*", Journal of Biological Chemistry, 1993, 268(4), 2571-2576.
Chu et al., "Retinoic acid induces Gpx2 gene expression in MCF-7 human breast cancer cells", The Journal of Nutrition, 1999, 129(10), 1846-1854.
Clark et al., "Long-acting growth hormones produced by conjugation with polyethylene glycol*", Journal of Biological Chemistry, 1996, 271(36), 21969-21977.
Copenheaver, Blaine R., PCT International Search Report and Written Opinion for Application No. PCT/US2015/045776, dated Dec. 21, 2015 (22 pages).
Copenheaver, Blaine R., PCT International Search Report and Written Opinion for Application No. PCT/US2015/045777, dated Dec. 29, 2015 (18 pages).
Copenheaver, Blaine R., PCT International Search Report and Written Opinion for Application No. PCT/US2016/021404 dated Jul. 8, 2016. (20 pages).
Czarnik, A.W., "Encoding methods for combinatorial chemistry", Current opinion in chemical biology, 1997, 1(1), 60-66.
Database WPI, Week 200954, Thomson Scientific, London GB; AN-2009-L88166, XP002778815, & KR 2009 0076254 A (Univ Kyunghee Ind Academic Coop Found) Jul. 13, 2009 (2 pages).
Deghenghi et al., "Gh-Releasing Activity of Hexarelin, A New Growth Hormone Releasing Peptide, in Infant and Adult Rats", Life Sciences, 1994, 54(18):1321-1328.
Dikmen et al., "Neuropsychological and psychosocial consequences of minor head injury", J Neurol Neurosurg Psychiatry, 1986, 49(11): p. 1227-1232.
Dikmen et al., "Neurobehavioral outcomes and their determinants", Journal of Head Trauma Rehabilitation, 1995, 10 (1): p. 74-86.
Dreborg, S. & Akerblom, E.B., "Immunotherapy with monomethoxypolyethylene glycol modified allergens", Critical Reviews in Therapeutic Drug Carrier Systems, 1990, 6(4), 315-365.
Duncan, R., "Soluble Synthetic Polymers as Potential Drug Carriers", Adv. Polym. Sci., 1984, 57:51-101.
Elipe Silva, et al. 1H NMR structural analysis of human ghrelin and its six truncated analogs. Biopolymers 59.7 (2001): 489-501.
Englander et al., "Mild traumatic brain injury in an insured population: subjective complaints and return to employment", Brain Injury, 1992, 6(2):161-166.
Giza, C. C., & Hovda, D. A. (2001). The neurometabolic cascade of concussion. Journal of athletic training, 36(3), 228-235.
Giza, C. C., et al.,(2014). The new neurometabolic cascade of concussion. Neurosurgery, 75(0 4), S24.-33.
Goody, R.S., & Eckstein, F., "Thiophosphate analogs of nucleoside di-and triphosphates", Journal of the American Chemical Society, 1971, 93(23), 6252-6257.
Gronwall et al., "Delayed recovery of intellectual function after minor head injury", Lancet, 1974, 2(7881): pp. 605-609.
Gronwall et al., "Memory and information processing capacity after closed head injury", J Neurol Neurosurg Psychiatry, 1981, 44(10):889-895.

Herlambang et al., "New method for absolute spinal cord ischemia protection in rabbits", J. Vasc. Surg., 2011 Oct., 54(4):1109-16, Epub. Sep 3, 2011.
Hinton-Bayre et al., "Concussion in contact sports: reliable change indices of impairment and recovery", J Clin Exp Neuropsychol, 1999, 21(1): 70-86.
Holm et al., "Summary of the WHO collaborating centre for neurotrauma task force on mild traumatic brain injury", J Rehabil Med, 2005, 37(3):137-41.
Hovda, D. A., "Oxidative need and oxidative capacity following traumatic brain injury", Crit. Care Med., 2007, 35 (2):663-4.
Howard et al., "A Receptor in Pituitary and Hypothalamus that Functions in Growth Hormone Release", Science, 1996, 273(5277):974-977.
Inui et al. "Ghrelin, appetite, and gastric motility: the emerging role of the stomach as an endocrine organ," Faseb J. Mar. 1, 2004, vol. 18, pp. 439-456.
Kelly et al., "Concussion in sports. Guidelines for the prevention of catastrophic outcome", JAMA, 1991, 266(20): 2867-2869.
Kil et al., "Ebselen treatment reduces noise induced hearing loss via the mimicry and induction of glutathione peroxidase", Hearing research, 2007, 226(1), 44-51.
Kojima, "Discovery of Ghrelin and its Physiological Function," J. Med. Sciences, (2010), 3(2):92-95.
Korek, Emilia et al., "Fasting and postprandial levels of ghreli, m leptin, and insulin in lean, obese, and anorexic subjects", Prz Gastroenterol. (2013) 8(6), pp. 383-389.
Levin et al., "The Galveston Orientation and Amnesia Test: A Practical Scale to Assess Cognition after Head Injury", Nervous Mental Dis, 1979, 167(11):675-84.
Lynch et al., "Ebselen-Mediated Protection From Single and Repeated Noise Exposure in Rat", The Laryngoscope, 2004, 114(2), 333-337.
Mannix, R., et., al. (2014). Serum biomarkers predict acute symptom burden in children after concussion: a preliminary study. Journal of neurotrauma, 31(11), 1072-1075.
Marmarou et al., "A new model of diffuse brain injury in rats: Part I: Pathophysiology and biomechanics", Journal of Neurosurgery, 1994, 80(2):291-300.
Matsumoto et al., "Structural similarity of ghrelin derivatives to peptidyl growth hormone secretagogues", Biochemical and biophysical research communications, 284(3), 655-659, 2001.
Matsumoto et al., "Structure—Activity Relationship of Ghrelin: Pharmacological Study of Ghrelin Peptides", Biochem. Biophys. Res. Commun., 2001, 287:142-146.
McCrory, P., et. al. (2013). Consensus statement on concussion in sport: the 4th International Conference on Concussion in Sport held in Zurich, Nov. 2012. British journal of sports medicine, 47(5), 250-258.
Mintz "Dln101 a naturally occurring ghrelin splice variant for the treatment of cachexia" 6th Cachexia Conference, Milan, Italy, Dec. 8, 2011, J Cachexia Sarcopenia Muscle, vol. 2, pp. 209-261.
Mrozek et al., "Biomarkers and acute brain injuries: interest and limits," Critical Care, Biomed Central Ltd., 2014, 18(2):220, pp. 1-12.
Mullenbach, G., et al., (1988). cDNAs of the three glutathione peroxidases: selenocysteine incorporation. Oxy—radicals in Molecular Biology and Pathology (P. Cerutti, I. Fridovich, and J. McCord, Eds.), Alan R. Liss, New York, 314-326.
NFL Concussion Tool, sports concussion assessment tool ("SCAT-2;" http://static.nfl.com/static/content/public/photo/2014/02/20/0ap2000000327062.pdf., 2009, 2 pages.
Ng, K. M E., & Orgel, L. E. "The action of a water-soluble carbodiimide on adenosine-5-'-polyphosphates", Nucleic acids research, 1987, 15(8), 3573-3580.
Nickitas-Etienne, Athina, PCT International Preliminary Report on Patentability (Chapter 1) for Application No. PCT/US2015/045776 dated Apr. 6, 2017. (17 pages).
Omalu et al, "Chronic Traumatic Encephalopathy in a National Football League Player", Neurosurgery, 2005, 57(1):128-34.
Omalu et al., "Chronic Traumatic Encephalopathy in a National Football League Player: Part II", Neurosurgery, 2006, 59(5):1086-92.

(56) References Cited

OTHER PUBLICATIONS

Ong, H., et al. (1998). Identification of a pituitary growth hormone-releasing peptide (GHRP) receptor subtype by photoaffinity labeling. Endocrinology 139.1, pp:432-435.

Palus et al. "Ghrelin and its Analogues, BIM-28131 and BIM-28125, Improve Body Weight and Regulate the Expression of MuRF-1 and MAFbx in a Rat Heart Failure Model," PloS ONE, Nov. 15, 2011, vol. 6, e26865, pp. 1-7.

Pang, S. N. J., "Final report on the safety assessment of polyethylene glycols (PEGs)-6,-8,-32,-75,-150,-14M,-20M", Journal of the American College of Toxicology, 1993, 12(5): 429-457.

Papotti, Mauro, et al. (2000) Growth hormone secretagogue binding sites in peripheral human tissues 1. The Journal of Clinical Endocrinology & Metabolism 85.10, pp: 3803-3807.

Polenzani, Sandrine, International Search Report and Written Opinion for Application No. PCT/US2016/059580 dated Jan. 30, 2017, 14 pages.

Rapaport et al., "HeLa cell DNA polymerase alpha is tightly associated with tryptophanyl-tRNA synthetase and diadenosine 5',5'''-P1,P4-tetraphosphate binding activities", Proc. Natl. Acad. Sci. U.S.A., 1981, 78(2):838-42.

Roveri et al., "Phospholipid hydroperoxide glutathione peroxidase of rat testis, Gonadotropin dependence and Immunocytochemical identification", Journal of Biological Chemistry, 1992, 267(9): 6142-6146.

Smith, D.B., & Johnson, K.S., "Single-step purification of polypeptides expressed in *Escherichia coli* as fusions with glutathione S-transferase", Gene, 1988, 67(1): 31-40.

Smith et al., "Growth Hormone Releasing Substances: Types and Their Receptors", Horm Res 1999;51(suppl 3):1-8.

Smith et al., "Peptidomimetic Regulation of Growth Hormone Secretion", Endocrine Reviews, 1997, 18(5): 621-645.

Smith, R.G., "Development of growth hormone secretagogues", Endocrine reviews, 2005, 26(3): 346-360.

Stuss, D.T. & Levine, B., "Adult Clinical Neuropsycholog: Lessons from Studies of the Frontal Lobes", Annual Review of Psychology, 2002, 53: 401-433.

Van Bregt, Daniel R., "Substantia nigra vulnerability after a single moderate diffuse brain injury in the rat", Exp. Neurol. (2012), 234(1), pp. 8-19.

Van Der Naalt, J., "Prediction of outcome in mild to moderate head injury: a review", Journal of Clinical & Experimental Neuropsychology, 2001, 23(6): 837-51.

Wigler et al., "Transfer of Purified Herpes Virus Thymidine Kinase Gene to Cultured Mouse Cells", Cell, 1977, 11:223-232.

Zamecnik, et al.(1982). Priming of DNA synthesis by diadenosine 5',5'''-P1, P4-tetraphosphate with a double-stranded octadecamer as a template and DNA polymerase alpha. Proceedings of the National Academy of Sciences, 79(6), 1791-1794.

Zhang et al., "Acute effect of Ghrelin on ischemia/reperfusion injury in the rat spinal cord", Int. J. Mol. Sci., 2012, 13(8):9864-76, Epub. Aug. 8, 2012.

SEQUENCE LISTING

<160> NUMBER OF SEQ ID NOS: 9

<210> SEQ ID NO 1
<211> LENGTH: 28
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: acylated with an octanoyl group
      (-CO-(CH2)6-CH3)
<220> FEATURE:
<221> NAME/KEY: MISC_FEATURE
<222> LOCATION: (3)..(3)
<223> OTHER INFORMATION: acylated with an octanoyl group
      (-CO-(CH2)6-CH3)

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 27
<212> TYPE: DNA
<213> ORGANISM: Artificial Sequence
<220> FEATURE:
<223> OTHER INFORMATION: gene specific primer flanking the full-length
      coding sequence of hGHS-R

<400> SEQUENCE: 2
atgtggaacg cgacgcccag cgaagag                                         27

<210> SEQ ID NO 3
<211> LENGTH: 27
<212> TYPE: DNA
<213> ORGANISM: Artificial Sequence
<220> FEATURE:
<223> OTHER INFORMATION: gene specific primer flanking the full-length
      coding sequence of hGHS-R

<400> SEQUENCE: 3
tcatgtatta atactagatt ctgtcca                                         27

<210> SEQ ID NO 4
<211> LENGTH: 20
<212> TYPE: PRT
<213> ORGANISM: Tilapia mossambica
<220> FEATURE:
<221> NAME/KEY: MISC_FEATURE
<222> LOCATION: (3)..(3)
<223> OTHER INFORMATION: acylated with an octanoyl group
      (-CO-(CH2)6-CH3)

<400> SEQUENCE: 4

Gly Ser Ser Phe Leu Ser Pro Ser Gln Lys Pro Gln Asn Lys Val Lys
1               5                   10                  15

Ser Ser Arg Ile
            20

<210> SEQ ID NO 5
<211> LENGTH: 28
<212> TYPE: PRT
<213> ORGANISM: Mus musculus

```
<220> FEATURE:
<221> NAME/KEY: MISC_FEATURE
<222> LOCATION: (3)..(3)
<223> OTHER INFORMATION: acylated with an octanoyl group
      (-CO-(CH2)6-CH3)

<400> SEQUENCE: 5

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 6
<211> LENGTH: 28
<212> TYPE: PRT
<213> ORGANISM: Sus barbatus
<220> FEATURE:
<221> NAME/KEY: MISC_FEATURE
<222> LOCATION: (3)..(3)
<223> OTHER INFORMATION: acylated with an octanoyl group
      (-CO-(CH2)6-CH3)

<400> SEQUENCE: 6

Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25

<210> SEQ ID NO 7
<211> LENGTH: 28
<212> TYPE: PRT
<213> ORGANISM: Platyrrhinus helleri
<220> FEATURE:
<221> NAME/KEY: MISC_FEATURE
<222> LOCATION: (3)..(3)
<223> OTHER INFORMATION: acylated with an octanoyl group
      (-CO-(CH2)6-CH3)

<400> SEQUENCE: 7

Gly Ser Ser Phe Leu Ser Pro Glu His Gln Arg Ala Gln Gln Arg Lys
1               5                   10                  15

Glu Ser Lys Lys Pro Pro Ala Lys Leu Gln Pro Arg
            20                  25

<210> SEQ ID NO 8
<211> LENGTH: 26
<212> TYPE: PRT
<213> ORGANISM: Gallus gallus
<220> FEATURE:
<221> NAME/KEY: MISC_FEATURE
<222> LOCATION: (3)..(3)
<223> OTHER INFORMATION: acylated with an octanoyl group
      (-CO-(CH2)6-CH3)

<400> SEQUENCE: 8

Gly Ser Ser Phe Leu Ser Pro Thr Tyr Lys Asn Ile Gln Gln Gln Lys
1               5                   10                  15

Asp Thr Arg Lys Pro Thr Ala Arg Leu His
            20                  25

<210> SEQ ID NO 9
<211> LENGTH: 28
<212> TYPE: PRT
<213> ORGANISM: Canis familiaris
```

```
<220> FEATURE:
<221> NAME/KEY: MISC_FEATURE
<222> LOCATION: (3)..(3)
<223> OTHER INFORMATION: acylated with an octanoyl group
      (-CO-(CH2)6-CH3)

<400> SEQUENCE: 9

Gly Ser Ser Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25
```

METHODS OF TREATING MILD BRAIN INJURY

CROSS-REFERENCE

This application is a U.S. National Stage Application filed under 35 U.S.C. § 371 and claims priority to International Application no. PCT/US2015/014692, filed Feb. 5, 2015, which claims the benefit of U.S. Provisional Application No. 61/936,143, filed Feb. 5, 2014 and which is a continuation in part of U.S. application Ser. No. 14/486,636, filed Sep. 15, 2014, each of which is incorporated herein by reference in its entirety.

FIELD OF THE INVENTION

This invention provides for methods for treating mild brain injuries and other neurological disorders arising from such an injury in a subject by administering to the subject an effective amount of a composition comprising ghrelin.

BACKGROUND OF THE INVENTION

Ghrelin, a 28-amino acid peptide predominantly secreted by gastric mucosa, is a neuroendocrine hormone that acts as an endogenous ligand for growth hormone secretagogue receptor. Beyond the known effects on hunger regulation, ghrelin is known to have potent anti-inflammatory properties and has been shown to be protective in several models of severe neuronal injury.

Post traumatic brain injury (i.e., TBI) edema and the complications associated with increased Intracranial pressure (ICP) account for approximately 50% of death in hospitalized patients. Medically managing intracranial hypertension utilizes a strategy combining sedation and osmotic agents such as mannitol and hypertonic saline. Knowing that ghrelin has potent anti-inflammatory effects, we have shown that ghrelin prevents blood brain barrier (BBB) permeability, intestinal dysfunction and systemic inflammation following TBI. The mechanism of these above observations are unclear, but may be, at least in part, a result of decreasing transcription of inflammatory cytokines and end-cascade effects including decreasing apoptosis, and blood brain barrier leakage. Ghrelin treated TBI animals had a significant decrease in brain fluorescence correlating with decreased BBB vascular permeability. We have shown that ghrelin prevents post-TBI up-regulation of Aquaporin 4 (AQP-4). Previous studies have shown that decreased expression of AQP-4 was associated with prevention of BBB breakdown and brain edema.

Mild brain injuries (mBI), typically including concussions, having "your bell rung", and the like, describe an insult to the brain that, in turn, can cause long term injury to the brain. To date, there has been little to no credible treatment of such mild brain injuries (mBI). Thus, there is a significant unmet need for a therapy for treating mBI that does not impose undesirable costs and delays and are effective.

SUMMARY OF THE INVENTION

This invention provides for methods of treating mild brain injury (mBI) in a subject having such an injury, comprising administering to the subject an effective amount of ghrelin or ghrelin agonist, thereby treating the mBI. In some embodiments, ghrelin comprises a polypeptide comprising at least one modification to the natural form of an amino acid sequence of Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg (SEQ ID NO. 1). In some instances, the serine at amino acid position 2 and/or serine at amino acid position 3 are/is acylated with an octanoyl group ($-C(O)(CH_2)_6CH_3$). Amino acids at position 1 to 5 of SEQ ID NO. 1 of the ghrelin or ghrelin agonist can have a modification. In some embodiments, ghrelin increases uncoupling protein-2 (UCP-2) expression. In some embodiments, ghrelin increases UCP-2 expression in mitochondria. The amount delivered according to the methods herein, can be for example, dosage of 2 μg/kg per dose and/or per day. In an embodiment of the invention, ghrelin is des-acyl-ghrelin or ghrelin with no modification of the primary amino acid sequence as provided in SEQ ID NO. 1. In another embodiment, ghrelin binds to a receptor other than GHSR-1a or ghrelin receptor, and wherein binding to a receptor other than GHSR-1a or ghrelin receptor provides a therapeutic benefit following mBI, for example, neuroprotection following mBI, repeated mBI or CTE. The therapeutic benefit such as neuroprotection following mBI or repeated mBI may include reduced oxidative stress or reduced apoptosis.

In some embodiments, the mild brain injury comprises a concussion. In some embodiments, the subject is a mammal. In some embodiments, the subject is a human. In some embodiments, ghrelin is administered within not more than about 8, 24 or 72 hours after the mBI. In some embodiments, ghrelin is administered within not more than about 24 hours after the mBI. In some embodiments, ghrelin is administered within or at about 0.1, 0.3, 0.5, 0.7, 1, 2, 3, 6, 8, 12, 18, 24, 36, 48, or 72 hours after the mBI.

This invention provides for methods of reducing the incidence or severity of mBI in a subject, comprising administering to the subject an effective amount of ghrelin, thereby reducing the incidence or severity of the mBI. In some embodiments, ghrelin is administered prior to an event or activity with a potential for occurrence of mBI.

This invention provides for methods of reducing the amount of time required for recovery from a mild brain injury, comprising administering to a patient suffering from a mild brain injury a therapeutically effective amount of ghrelin within 72 hours of the mild brain injury. In some embodiments, ghrelin is administered in a single dose. In some embodiments, ghrelin is administered at a dosage from 10 ng/kg per day to 10 mg/kg per day.

Still further, ghrelin can be used in an assay to assess the ability of candidate compounds to effect increased uncoupling protein-2 (UCP-2) expression including increased UCP-2 expression in mitochondria. In such assays, ghrelin is used as a control to determine the relative efficacy of the candidate compound or compounds. Suitable assays include, by way of example only, competitive assays for binding of a candidate compound or compounds to growth hormone secretagogue receptor 1a (i.e., GHSR) in the presence of ghrelin as well as frontal affinity chromatography.

In yet another embodiment, a patient suffering loss of cognitive or motor skills due to mBI and, in particular, repetitive mBI, can be monitored for therapy or progression of such skills by correlating the ghrelin level in the patient's brain over time. As the ghrelin levels decrease, there will be an increased need for intervention. This invention also provides for methods of measuring ghrelin levels before an activity, for example before the start of football, soccer, rugby or any other sport or activity season, and monitoring during the season to ascertain if the player is at a level not qualified to play or participate by utilizing a test or an assay for measuring ghrelin levels, such as a test or assay for determining levels in the blood.

In some embodiments, the present invention provides for a method for treating a subject suffering from metabolic derangements associated with mBI or concussion, wherein such method comprises administration of an effective amount of ghrelin to the subject, thereby treating the subject suffering from metabolic derangements associated with mBI or concussion.

In some embodiments, the present invention provides for a method for treating a subject suffering from increased levels of reactive oxidative species (ROS) in neurons associated with mBI or concussion, wherein such method comprises administration of an effective amount of ghrelin to the subject so as to decrease levels of ROS in neurons associated with mBI or concussion, thereby treating the subject suffering from metabolic derangements associated with mBI or concussion.

In some embodiments, the present invention provides for a method for preventing chronic traumatic encephalopathy (CTE) associated with repeated mBI or concussions in a subject, wherein such method comprises administration of one or more doses of ghrelin to the subject, thereby preventing chronic traumatic encephalopathy (CTE) associated with repeated mBI or concussions in a subject.

In some embodiments, the present invention provides for a method for preventing damage to neurons associated with oxidative stress and overproduction of reactive oxidative species (ROS) in a subject with one or more incidence of mBI or concussion, wherein such method comprises administration of one or more doses of ghrelin to the subject, thereby preventing damage to neurons associated with oxidative stress and overproduction of reactive oxidative species (ROS) in a subject with one or more incidence of mBI or concussion.

In some embodiments, the present invention provides for a method for treating injured or disrupted neuronal or axonal connection in the brain of a subject with one or more incidence of mBI, including concussion, wherein such method comprises administration of one or more doses of ghrelin to the subject, thereby treating injured or disrupted neuronal or axonal connection in the brain of a subject with one or more incidence of mBI, including concussion. In one embodiment, the injured or disrupted neuronal or axonal connection is mechanical disruption of neuronal or axonal cytoskeleton. In another embodiment, the injured or disrupted neuronal or axonal connection is disruption or altered neuronal or axonal transport. In another embodiment, the injured or disrupted neuronal or axonal connection is proteolysis, die-back disconnection and reorganization. In one embodiment, treating injured or disrupted neuronal or axonal connection in the brain of a subject with one or more incidence of mBI, including concussion, restores neuronal or axonal connection in the brain of a subject following one or more incidence of mBI, including concussion. In another embodiment, treating injured or disrupted neuronal or axonal connection in the brain of a subject with one or more incidence of mBI or concussion hastens restoration of neuronal or axonal connection in the brain of a subject following one or more incidence of mBI, including concussion.

In some embodiments, the present invention provides for a method for preventing or diminishing occurrence of an injured or disrupted neuronal or axonal connection in the brain of a subject with one or more incidence of mBI, including concussion, wherein such method comprises administration of one or more doses of ghrelin to the subject, thereby reducing or preventing or diminishing occurrence of an injured or disrupted neuronal or axonal connection in the brain of a subject with one or more incidence of mBI, including concussion. In one embodiment, the injured or disrupted neuronal or axonal connection is mechanical disruption of neuronal or axonal cytoskeleton. In another embodiment, the injured or disrupted neuronal or axonal connection is disruption or altered neuronal or axonal transport. In another embodiment, the injured or disrupted neuronal or axonal connection is proteolysis, die-back disconnection and reorganization. In one embodiment, ghrelin is administered prior to the occurrence of one or more incidence of mBI, including concussion. In another embodiment, ghrelin is administered immediately after the occurrence of an mBI, including concussion. In another embodiment, ghrelin is administered prior to and following occurrence of one or more mBI, including concussion. In another embodiment, multiple doses of ghrelin are administered.

In some embodiments, the present invention provides for a method for treating perturbed brain physiology in a subject with one or more incidence of mBI, including concussion, wherein such method comprises administration of one or more doses of ghrelin to the subject so as to restore normal neuronal depolarization, thereby treating perturbed brain physiology in a subject with one or more incidence of mBI, including concussion. In one embodiment, treating perturbed brain physiology with ghrelin restores normal brain physiology. In another embodiment, treating perturbed brain physiology with ghrelin hastens restoration of normal brain physiology.

In some embodiments, the present invention provides for a method for preventing perturbed brain physiology in a subject with one or more incidence of mBI, including concussion, wherein such method comprises administration of one or more doses of ghrelin to the subject so as to maintain normal neuronal depolarization, thereby reducing or preventing perturbed brain physiology in a subject with one or more incidence of mBI, including concussion. In one embodiment, ghrelin is administered prior to the occurrence of one or more incidence of mBI, including concussion. In another embodiment, ghrelin is administered immediately after the occurrence of an mBI, including concussion. In another embodiment, ghrelin is administered prior to and following occurrence of one or more mBI, including concussion. In another embodiment, multiple doses of ghrelin are administered.

In some embodiments, the present invention provides for a method for treating perturbed brain physiology in a subject with one or more incidence of mBI or concussion, wherein such method comprises administration of one or more doses of ghrelin to the subject so as to restore normal release of excitatory neurotransmitters, thereby treating perturbed brain physiology in a subject with one or more incidence of mBI or concussion. In one embodiment, treating perturbed brain physiology with ghrelin restores normal brain physiology. In another embodiment, treating perturbed brain physiology with ghrelin hastens restoration of normal brain physiology.

In some embodiments, the present invention provides for a method for preventing perturbed brain physiology in a subject with one or more incidence of mBI or concussion, wherein such method comprises administration of one or more doses of ghrelin to the subject so as to maintain normal release of excitatory neurotransmitters, thereby reducing or preventing perturbed brain physiology in a subject with one or more incidence of mBI or concussion. In one embodiment, ghrelin is administered prior to the occurrence of one or more incidence of mBI or concussion. In another embodiment, ghrelin is administered immediately after the occurrence of an mBI or concussion. In another embodiment, ghrelin is administered prior to and following occurrence of one or more mBI or concussion. In another embodiment, multiple doses of ghrelin are administered.

In some embodiments, the present invention provides for a method for treating perturbed brain physiology in a subject with one or more incidence of mBI or concussion, wherein such method comprises administration of one or more doses of ghrelin to the subject so as to restore normal cerebral blood flow, thereby treating perturbed brain physiology in a subject with one or more incidence of mBI or concussion. In one embodiment, treating perturbed brain physiology with ghrelin restores normal brain physiology. In another embodiment, treating perturbed brain physiology with ghrelin hastens restoration of normal brain physiology.

In some embodiments, the present invention provides for a method for preventing perturbed brain physiology in a subject with one or more incidence of mBI or concussion, wherein such method comprises administration of one or more doses of ghrelin to the subject so as to maintain normal cerebral blood flow, thereby reducing or preventing perturbed brain physiology in a subject with one or more incidence of mBI or concussion. In one embodiment, ghrelin is administered prior to the occurrence of one or more incidence of mBI or concussion. In another embodiment, ghrelin is administered immediately after the occurrence of an mBI or concussion. In another embodiment, ghrelin is administered prior to and following occurrence of one or more mBI or concussion. In another embodiment, multiple doses of ghrelin are administered.

In some embodiments, the present invention provides for a method for treating perturbed brain physiology in a subject with one or more incidence of mBI or concussion, wherein such method comprises administration of one or more doses of ghrelin to the subject so as to restore proper or normal axonal function, thereby treating perturbed brain physiology in a subject with one or more incidence of mBI or concussion. In one embodiment, treating perturbed brain physiology with ghrelin restores normal brain physiology. In another embodiment, treating perturbed brain physiology with ghrelin hastens restoration of normal brain physiology.

In some embodiments, the present invention provides for a method for preventing perturbed brain physiology in a subject with one or more incidence of mBI or concussion, wherein such method comprises administration of one or more doses of ghrelin to the subject so as to maintain proper or normal axonal function, thereby reducing or preventing perturbed brain physiology in a subject with one or more incidence of mBI or concussion. In one embodiment, ghrelin is administered prior to the occurrence of one or more incidence of mBI or concussion. In another embodiment, ghrelin is administered immediately after the occurrence of an mBI or concussion. In another embodiment, ghrelin is administered prior to and following occurrence of one or more mBI or concussion. In another embodiment, multiple doses of ghrelin are administered.

In some embodiments, the present invention provides for a method for treating perturbed brain physiology in a subject with one or more incidence of mBI or concussion, wherein such method comprises administration of one or more doses of ghrelin to the subject so as to restore brain metabolic function, thereby treating perturbed brain physiology in a subject with one or more incidence of mBI or concussion. In one embodiment, treating perturbed brain physiology with ghrelin restores normal brain physiology. In another embodiment, treating perturbed brain physiology with ghrelin hastens restoration of normal brain physiology.

In some embodiments, the present invention provides for a method for preventing perturbed brain physiology in a subject with one or more incidence of mBI or concussion, wherein such method comprises administration of one or more doses of ghrelin to the subject so as to maintain brain metabolic function or balance, thereby reducing or preventing perturbed brain physiology in a subject with one or more incidence of mBI or concussion. In one embodiment, ghrelin is administered prior to the occurrence of one or more incidence of mBI or concussion. In another embodiment, ghrelin is administered immediately after the occurrence of an mBI or concussion. In another embodiment, ghrelin is administered prior to and following occurrence of one or more mBI or concussion. In another embodiment, multiple doses of ghrelin are administered.

In some embodiments, the present invention provides for a method for treating perturbed brain physiology in a subject with one or more incidence of mBI or concussion, wherein such method comprises administration of one or more doses of ghrelin to the subject so as to restore glucose metabolism, thereby treating perturbed brain physiology in a subject with one or more incidence of mBI or concussion. In one embodiment, treating perturbed brain physiology with ghrelin restores normal brain physiology. In another embodiment, treating perturbed brain physiology with ghrelin hastens restoration of normal brain physiology.

In some embodiments, the present invention provides for a method for preventing perturbed brain physiology in a subject with one or more incidence of mBI or concussion, wherein such method comprises administration of one or more doses of ghrelin to the subject so as to maintain glucose metabolism, thereby reducing or preventing perturbed brain physiology in a subject with one or more incidence of mBI or concussion. In one embodiment, ghrelin is administered prior to the occurrence of one or more incidence of mBI or concussion. In another embodiment, ghrelin is administered immediately after the occurrence of an mBI or concussion. In another embodiment, ghrelin is administered prior to and following occurrence of one or more mBI or concussion. In another embodiment, multiple doses of ghrelin are administered.

In some embodiments, the present invention provides for a method for preventing memory loss or headaches in a subject with mBI or concussion, wherein such method comprises administration of an effective amount of ghrelin to the subject in one or more doses, thereby preventing memory loss and/or headaches in a subject with mBI or concussion.

Some embodiments relate to formulations for administration to a subject, which formulations can include a pharmaceutically acceptable carrier and ghrelin having a carbon 14 (C14) content of less than 1 part per trillion (ppt), wherein said formulation is suitable for delivery of an effective amount of ghrelin to the brain of said patient so as to treat mild brain injuries. For example, any of the methods described above and elsewhere herein can utilize a ghrelin molecule have a C14 content of less than 1 ppt.

Some embodiments relate to methods of monitoring a mild brain injury, the severity of an injury and/or the recovery from such an injury. The methods can include, for example, administering a purified ghrelin compound, including for example, ghrelin with a C14 content of less than 1 ppt, in a pharmaceutically acceptable composition to a subject that has suffered a mild brain injury.

Some embodiments relate to methods of treating mild brain injury, reducing the incidence or severity of mBI in a subject, and/or reducing the amount of time needed to recover from a mild brain injury. The methods include providing or administering to a subject in need (e.g., a subject that has suffered, is at risk of suffering, is prone to suffer, and/or is about to participate in an activity with a high risk for suffering, a mBI) an amount of ghrelin (including ghrelin with a C14 content of less than 1 ppt) sufficient to provide a therapeutically effective in vivo level of ghrelin to treat or reduce according to the method, wherein the level is greater than the endogenous level of ghrelin in the subject. For example, the amount of administered ghrelin can be an amount sufficient to provide a blood level of ghrelin that is greater than the usual or average endogenous blood level of ghrelin, such as 1.5, 2, 3, 5, 10, 20, 50, 100, 1,000 or up to 2,000 times the normal endogenous blood level (or any sub value or sub range there between). In some case, the amount administered can result in a blood or plasma concentration of at least 55 picograms per milliliter. In some embodiments the greater ghrelin levels can be achieved within hours of the injury (e.g., less than 8 hours after the injury). They also can be maintained above endogenous levels for some period of time that is sufficient to provide the desired therapeutic benefit, for example, for at least 30 minutes to 24 hours (or any sub value or sub range there between). Endogenous ghrelin levels are not sufficient for treating mBI or reducing the incidence, severity or the time needed to recover as readily evidenced by the long term damage done to the brain by repetitive concussive injuries (mBI). The instant embodiments provide a benefit and result that do not occur naturally in the body with endogenous levels. Such a benefit was unknown prior to the instant embodiments associated with the invention. In some embodiments, the methods can further include selecting or identifying a subject that has suffered, is at risk of suffering, is prone to suffer, and/or is about to participate in an activity with a high risk for suffering, a mBI, prior to administration of the ghrelin.

Some embodiments relate to methods for determining the efficacy of a compound treating a patient suffering mild brain injury (mBI). The methods can include, for example, i) determining the expression level of uncoupling protein-2 (UCP-2) in a biological sample obtained from the patient treated with the compound; ii) comparing the expression level of UCP-2 to a biological sample obtained from a subject treated with ghrelin (as described herein including with the modifications described herein); and iii) determining the efficacy of the compound, wherein the compound is efficacious when the expression level of UCP-2 induced by the compound is equal to (within at least 10%) or greater than the expression level of UCP-2 induced by ghrelin.

Some embodiments relate to methods for treating a patient suffering loss of cognitive or motor skills due to mild brain injury (mBI). The methods can include, for example, i) determining the level of ghrelin in the patient's brain over a period of time; ii) administering ghrelin (including the modified and C14 versions described herein) to the patient; and iii) periodically repeating step ii) during treatment when the level of ghrelin falls below a normal range as a basis to determine the efficacy of the treatment, wherein an increase in the level of ghrelin in the brain demonstrates an improvement in the patient's cognitive or motor skill condition.

BRIEF DESCRIPTION OF THE DRAWINGS

The embodiments of this disclosure are drawings which illustrate by exemplification only, and not limitation, wherein.

Figure 1:
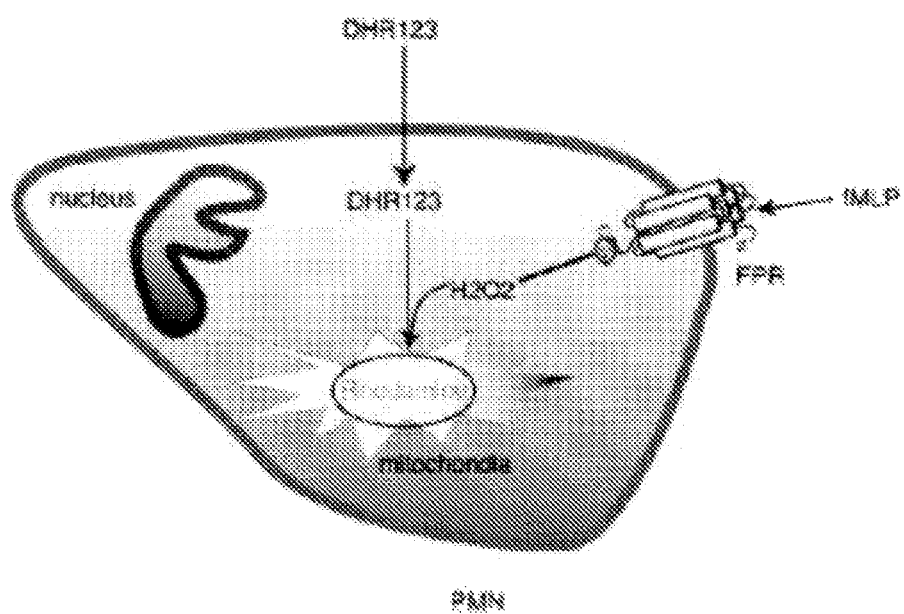
FIG. 1 depicts principle of assaying oxidative burst within inflammatory cells. Dihydrorhodamine 123 (DHR 123) diffuses across the cell membrane. When it encounters reactive oxygen species (ROS), DHR 123 is oxidized and fluoresces green. The fluorescence is then measured and presented as arbitrary fluorescence unit (AFU), wherein higher intensity means greater oxidative burst and, therefore greater concentration of amount of ROS (See Chen, et al., Measurement of oxidative burst in neutrophils," Methods Mol Biol., 844: 115-124 (2012); which is incorporated herein by reference in its entirety).

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION OF THE INVENTION

It is to be understood that the present disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

The detailed description of the present disclosure is divided into various sections only for the reader's convenience and disclosure found in any section may be combined with that in another section. Unless defined otherwise, all technical and scientific terms used herein have the same meaning as commonly understood by one of ordinary skill in the art to which the present disclosure belongs.

Definitions

It must be noted that as used herein and in the appended claims, the singular forms "a", "an", and "the" include plural referents unless the context clearly dictates otherwise. Thus, for example, reference to "a compound" includes a plurality of compounds.

Unless defined otherwise, all technical and scientific terms used herein have the same meaning as commonly understood by one of ordinary skill in the art to which the present disclosure belongs. As used herein the following terms have the following meanings.

As used herein, the term "about" when used before a numerical designation, e.g., temperature, time, amount, concentration, and such other, including a range, indicates approximations which may vary by (+) or (−) 10%, 5% or 1%.

As used herein, the term "administration" can be effected in one dose, continuously or intermittently or by several subdoses which in the aggregate provide for a single dose. Dosing can be conducted throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include oral administration, vaginal, nasal administration, injection, topical application, sublingual, pulmonary, and by suppository.

As used herein, the term "affinity" refers to the strength of binding between receptors and their ligands, for example, between an antibody and its antigen.

As used herein, the term "amino acid residue" refers to an amino acid formed upon chemical digestion (hydrolysis) of a polypeptide at its peptide linkages. Unless otherwise specified, the amino acid encompasses L-amino acid, including both natural amino acid and synthetic amino acid or the like as long as the desired functional property is retained by the polypeptide. $NH_2$ refers to the free amino group present at the amino terminus of a polypeptide. COOH refers to the free carboxy group present at the carboxy terminus of a polypeptide. Standard polypeptide abbreviations for amino acid residues are as follows: A (Ala or Alanine); C (Cys or Cysteine); D (Asp or Aspartic Acid); E (Glu or Glutamic Acid); F (Phe or Phenylalanine); G (Gly or Glycine); H (His or Histidine); I (Ile or Isoleucine); K (Lys or Lysine); L (Leu or Leucine); M (Met or Methionine); N (Asn or Asparagine); P (Pro or Proline); Q (Gln or Glutamine); R (Arg or Arginine); S (Ser or Serine); T (Thr or Threonine); V (Val or Valine); W (Trp or Tryptophan); X (Xaa or Unknown or Other); Y (Tyr or Tyrosine); and Z (Glx/Gln/Glu or Glutamic Acid/Glutamine). All amino acid residue sequences represented herein by formula have a left-to-right orientation in the conventional direction of amino terminus to carboxy terminus. The phrase "amino acid residue" is broadly defined to include the naturally occurring and modified and non-naturally occurring amino acids. A dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

As used herein, the terms "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the present disclosure. "Consisting of" shall mean excluding more than trace elements of other ingredients and substantial method steps. Embodiments defined by each of these transition terms are within the scope of the present disclosure.

As used herein, the term "ghrelin" is a polypeptide that may have 28 amino acid sequence as set forth in SEQ ID No. 1, and can include the octanoyl acylation as described above. Human ghrelin may be a polypeptide having the amino acid sequence as set forth in GenBank® Accession No. NP_057446 or Swiss-Prot Identifier GHRL_HUMAN. Human ghrelin preprotein has 117 amino acids. This preprotein may undergo the following post-translational processing. The signal peptide (amino acids 1-23) is removed and the remaining 94 amino acids are cleaved by a protease to provide a mature 28 amino acid ghrelin (amino acids 24-51) or a mature 27 amino acid ghrelin (amino acids 24-50) and a mature 23 amino acid obestatin (amino acids 76-98). In another embodiment, ghrelin comprises a polypeptide comprising at least one modification to the natural form of an amino acid sequence of Gly-Ser-Ser-Phe-Leu-Ser-Pro-Ser-Gln-Lys-Pro-Gln-Asn-Lys-Val-Lys-Ser-Ser-Arg-Ile (e.g., SEQ ID NO. 4). In another embodiment, ghrelin comprises a polypeptide comprising at least one modification to the natural form of an amino acid sequence of Gly-Ser-Ser-Phe-Leu-Ser-Pro-Glu-His-Gln-Lys-Ala-Gln-Gln-Arg-Lys-Glu-Ser-Lys-Lys-Pro-Pro-Ala-Lys-Leu-Gln-Pro-Arg (SEQ ID NO. 5). In another embodiment, ghrelin comprises a polypeptide comprising at least one modification to the natural form of an amino acid sequence of Gly-Ser-Ser-Phe-Leu-Ser-Pro-Glu-His-Gln-Lys-Val-Gln-Gln-Arg-Lys-Glu-Ser-Lys-Lys-Pro-Ala-Ala-Lys-Leu-Lys-Pro-Arg (SEQ ID NO. 6). In another embodiment, ghrelin comprises a polypeptide comprising at least one modification to the natural form of an amino acid sequence of Gly-Ser-Ser-Phe-Leu-Ser-Pro-Glu-His-Gln-Arg-Ala-Gln-Gln-Arg-Lys-Glu-Ser-Lys-Lys-Pro-Pro-Ala-Lys-Leu-Gln-Pro-Arg (SEQ ID NO. 7). In another embodiment, ghrelin comprises a polypeptide comprising at least one modification to the natural form of an amino acid sequence of Gly-Ser-Ser-Phe-Leu-Ser-Pro-Thr-Tyr-Lys-Asn-Ile-Gln-Gln-Gln-Lys-Asp-Thr-Arg-Lys-Pro-Thr-Ala-Arg-Leu-His (SEQ ID NO. 8). In yet another embodiment, ghrelin comprises a polypeptide comprising at least one modification to the natural form of an amino acid sequence of Gly-Ser-Ser-Phe-Leu-Ser-Pro-Glu-His-Gln-Lys-Leu-Gln-Gln-Arg-Lys-Glu-Ser-Lys-Lys-Pro-Pro-Ala-Lys-Leu-Gln-Pro-Arg (SEQ ID NO. 9). Modifications to ghrelin may include adding or removing amino acids so long as the ghrelin so modified retains its therapeutic value (e.g., by adding or removing any of 1, 2, 3, 4 or 5 amino acids from the molecule).

Some embodiments relate to and can utilize ghrelin molecules that have a carbon 14 (C14) content less than found in endogenously produced ghrelin molecules or in ghrelin that has a C14 content about the same as atmospheric C14 levels. For example, ghrelin molecules can have at least one carbon atom or carbon containing moiety that is from fossil derived reagents that have a C14 content less than found in endogenous molecules or less than atmospheric levels. In some embodiments, the ghrelin molecules can have all, substantially all or at least a some carbon having a C14 content less than found endogenously or less than atmospheric levels. For example, one or more of the amino acids of a sequence can include carbon and have a C14 content less than found in endogenous amino acids or less than atmospheric levels. In other cases an entire sequence can include carbon and have a C14 content less than found endogenously or less than atmospheric levels. Still, in other embodiments, a ghrelin molecule can be modified, for example to have an octanoyl or other like group, and that octanoyl group can have a C14 content less than endogenous ghrelin C14 levels or less than atmospheric levels. Further examples and embodiments are described below and elsewhere herein.

In some embodiments, ghrelin molecule can have a C14 content of less than 0.9 ppt, 0.95 ppt, 1.05 ppt, 1.10 ppt, 1.15 ppt, 1.2 ppt or atmospheric content of C14. In some embodiments, ghrelin molecule can have a C14 content that is from about 1% to 50% (or any value or sub range therein) less than the content of C14 in endogenous ghrelin or the content of atmospheric C14. For example, a molecule according to some embodiments can have about 5% to about 11% less C14 content. Ghrelin with C14 content of less than 0.9 ppt, 0.95 ppt, 1.0 ppt, 1.05 ppt, 1.10 ppt, 1.15 ppt, 1.2 ppt or atmospheric content of C14, or with a lesser percentage of C14 as discussed herein, may be obtained by peptide or chemical synthesis using reactants with carbons free of C14, less than 1 ppt C14 or deficient in C14 relative to the atmospheric content of C14. Alternatively, ghrelin with C14 content of less than 0.9 ppt, 0.95 ppt, 1.0 ppt, 1.05 ppt, 1.10 ppt, 1.15 ppt, 1.2 ppt or atmospheric content of C14 may be produced in vitro by enzymatic methods using starting materials with a carbon content free of C14, substantially free of C14, less than 1 ppt C14 or deficient in C14 relative to the atmospheric content of C14. Such enzymatic methods may include cell-free protein synthesis system or coupled in vitro transcription-translation system based on cellular extracts prepared from bacteria, yeast, wheat germ, insect and/or mammalian cells using aminoacyl-tRNAs charged with amino acids with a carbon content free of C14, substantially free of C14, less than 1 ppt C14 or deficient in C14 relative to the atmospheric content of C14. In an alternative method, ghrelin with C14 content of less than 0.9 ppt, 0.95 ppt, 1.0 ppt, 1.05 ppt, 1.10 ppt, 1.15 ppt, 1.2 ppt or atmospheric content of C14 may be produced by recombinant methods in bacterial, yeast, insect and/or mammalian cells following introduction of an expression system with a cDNA comprising ghrelin-encoded sequences and culturing the cells in a medium with a carbon content free of C14, substantially free of C14, less than 1 ppt C14 or deficient in C14 relative to the atmospheric content of C14. Alternatively, the medium may include glucose, galactose, sugars, glycerol, pyruvate, acetates, metabolites, fatty acids, and/or amino acids with a carbon content free of C14, substantially free of C14, less than 1 ppt C14 or deficient in C14 relative to the atmospheric content of C14. Methods for changing stable isotopic content of proteins may be found in Becker et al., 2008 (G. W. Becker (2008) Stable isotopic labeling of proteins for quantitative proteomic applications. Briefings in Functional Genomics Proteins 7 (5): 371-382, which is incorporated herein by reference in its entirety) Ghrelin may be co-expressed with or exposed to ghrelin O-acyl transferase (GOAT) to permit fatty acid modification of the primary sequence of ghrelin at serine at amino acid position 3 so as to produce a biologically active ghrelin capable of being bound and activating the ghrelin receptor (GHSR-1a or growth hormone secretagogue receptor type 1a). The modification may be an octanoic acid modification of ghrelin so as to produce octanoyl-ghrelin with a carbon content free of C14, substantially free of C14, less than 1 ppt C14 or deficient in C14 relative to the atmospheric content of C14.

In some embodiments, ghrelin with C14 content of less than 0.9 ppt, 0.95 ppt, 1.0 ppt, 1.05 ppt, 1.10 ppt, 1.15 ppt, 1.2 ppt or atmospheric content of C14 (or having a percentage as discussed herein) may be obtained following modification of the primary sequence of ghrelin (SEQ ID NO. 1) with a fatty acid with a carbon content free of C14, substantially free of C14, less than 1 ppt C14 or deficient in C14 relative to the atmospheric content of C14. Such fatty acids may be chemically synthesized with a carbon content free of C14, substantially free of C14, less than 1 ppt C14 or deficient in C14 relative to the atmospheric content of C14 or produced in a cell cultured in a medium wherein carbon source used to synthesize the fatty acid or fatty acids is free of C14, substantially free of C14, less than 1 ppt C14 or deficient in C14 relative to the atmospheric content of C14. In some embodiments, the fatty acid or fatty acids are conjugated to coenzyme A (CoA) and the fatty acid in the resulting fatty acid-CoA thioesters is transferred to serine at amino acid position 3 of ghrelin by ghrelin O-acyl transferase (GOAT), so as to produce a fatty acid-modified ghrelin with a carbon content free of C14, substantially free of C14, less than 1 ppt C14 or deficient in C14 relative to the atmospheric content of C14. In some embodiments, fatty acids are straight chain fatty acids with a carbon content of C2, C3, C4, C5, C6, C7, C8, C9, C10, C11, C12, C13, C14, C15, C16, C17, C18, C19 or C20 and having a general chemical formula of $(CH)_3—(CH_2)_{n-2}—COOH$, wherein "n" is the number of carbons in the fatty acid. In a preferred embodiment, the fatty acid is a C8 octanoic acid or C14 tetradecanoic acid. In a more preferred embodiment, the fatty acid is octanoic acid and the fatty acid-modified ghrelin is octanoyl-modified ghrelin at serine amino acid position 3.

In some embodiments, fatty acid or fatty acids may be conjugated to ghrelin at serine amino acid position 3. In some embodiments, fatty acid or fatty acids may be conjugated to ghrelin at a position other than serine amino acid position 3. In some embodiments, fatty acid or fatty acids may be conjugated to ghrelin at serine amino acid position 2. In some embodiments, fatty acid or fatty acids may be conjugated to ghrelin at serine amino acid position 2 and serine amino acid position 3. In some embodiments, fatty acid or fatty acids may be conjugated to ghrelin at one or more amino acids.

In some embodiments, fatty acid or fatty acids may be conjugated to immature ghrelin (such as preproghrelin or proghrelin) and then fatty acid- or fatty acids-modified ghrelin is processed to a mature ghrelin that can activate the ghrelin receptor (GHSR-1a). Processing of immature ghrelin may be in vitro or in vivo and may be carried out by proteolytic enzymes. In some embodiments, fatty acid or fatty acids may be conjugated to a mature ghrelin having the amino acid sequence as provided in SEQ ID NO. 1.

In some embodiments, ghrelin with one or more modifications is an isolated ghrelin with one or more modifications. In a preferred embodiment, ghrelin with one or more modifications is an isolated ghrelin with one or more fatty acid modifications. In a more preferred embodiment, ghrelin with one or more modifications is an isolated ghrelin acylated at serine 3 with octanoic acid, such as an isolated octanoyl-ghrelin.

C14-deficient starting material used in the synthesis of ghrelin with a carbon content free of C14, substantially free of C14, less than 1 ppt C14 or deficient in C14 relative to the atmospheric content of C14 may be obtained from carbon sources not participating in atmospheric carbon cycle or by fractionating naturally occurring carbon isotope to obtain carbons free of C14, substantially free of C14, less than 1 ppt C14 or deficient in C14 relative to the atmospheric content of C14. Such carbons will be enriched in carbon-12 (C12) and/or carbon-13 (C13) and depleted of C14. Methods for isotope fractionation, enrichment or depletion are known in the art and may be based on diffusion, centrifugation, electromagnetism, laser excitation, kinetic isotope effect, chemical methods, gravity, evaporation, and cryogenic distillation among many other methods of isotope fractionation.

The ghrelin as used in the various embodiments described herein can be any suitable ghrelin, including for example, ghrelin that is produced using recombinant methods and ghrelin that is chemically synthesized. Regardless of the source, the ghrelin can be used and administered as described herein. The ghrelin can be isolated ghrelin, for example, ghrelin obtained following fractionation or separation of ghrelin away from other constituents present in a sample in which ghrelin is produced or synthesized as well as modified. The isolated ghrelin need not be pure ghrelin. While it is desirable to have pure ghrelin or essentially pure ghrelin, isolated ghrelin may be used without achieving absolute purity so long as ghrelin has been fractionated or separated away from constituents whose presence is not desirable in a preparation of the isolated ghrelin. It is noted that following fractionation of ghrelin, the ghrelin may be introduced into solution or used as a mixture or admixture in the presence of other components such as pharmaceutical carrier(s), lubricant(s), preservative(s), buffer(s), salt(s), sugar(s), colorant(s), pharmaceutically acceptable excipient(s) and combination thereof.

As used herein, the term "ghrelin receptor" refers to any naturally occurring molecule to which ghrelin binds and induces a biological activity. Ghrelin is known to bind to growth hormone secretagogue receptor 1a (i.e., GHSR), however, the present disclosure is not limited to a specific type of receptor.

As used herein, the term "individual" or "subject" is an animal or human susceptible to a condition, in particular mBI or concussion. In some embodiments, the individual is a mammal, including human and non-human mammals such as dogs, cats, pigs, cows, sheep, goats, horses, rats, and mice.

As used herein, the term "mild brain injury" (mBI) sometimes referred as a "mild traumatic brain injury" (mTBI) refers to a non-disease event commonly caused by an injury resulting in an insult to the brain. mBI may be caused, for example, by impact forces, in which the head strikes or is struck by something, or impulsive forces, in which the head moves without itself being subject to blunt trauma (for example, when the chest hits something and the head snaps forward; as a result of rapid acceleration or deceleration of the head; acceleration or deceleration of the brain of a subject producing a change in a qualitative or quantifiable clinical parameter related to functional well-being of the subject; or differential acceleration or deceleration of the brain of the subject relative to the skull of the subject wherein differential acceleration or deceleration produces a change in a qualitative or quantifiable clinical parameter related to functional well-being of the subject). mBI commonly results, for example, from a sports-related injury, a motor vehicle accident, an accidental fall, or an assault. Although the vast majority of such injuries improve through natural recovery the damage caused by such an injury or repetitive injuries can cause long term deficits in cognitive and/or motor skill functions.

Mild BI is different from and has a distinct pathology as compared to diseases such as acute traumatic brain insults such as strokes (ischemic or hemorrhagic), AVM's, brain tumors, and the like.

Moreover, mBI is distinct from severe TBI. Mild brain injury and severe traumatic brain injury are dramatically different injuries. Mild BI and severe TBI have different characteristic and symptoms, different mortality rates, different treatment protocols, etc. Severe TBI is an injury state where there is an unacceptable level of mortality and permanent disability in humans within hours or days of the injury. According to the Centers for Disease Control, such injuries are a contributing factor to a third (30%) of all injury-related deaths in the United States (See, National Vital Statistics System (NVSS), 2006-2010). Severe TBIs often are caused, for example, by automobile accidents and combat gunshot and bomb wounds to the head. Severe TBI typically has direct and overt brain hemorrhage, brain cell destruction, severe brain edema and severe cellular apoptosis, all characteristic of anatomical changes or anatomical injury to the brain of the injured patient—all of which can be detected by non-invasive anatomical imaging methods. Due to the severity of such symptoms and risk of imminent death and disability, operative intervention and critical care are paramount. Severe TBI results in adverse anatomical changes in the patient's brain (observable at a gross anatomy level) resulting in immediate and permanent loss of brain function, if not death.

On the other hand, mild brain injury (mBI) causes changes in the brain function at a metabolic/molecular level in the affected neurons. As such, it does not typically cause mortality or permanent disability in the time frame provided above and patients often resume normal activities of daily living and functionality within hours or days of the mBI.

The body's response to severe TBI consists of a large number of differing responses including those initiated by hypoxia, blood loss and significant neuron death, to name just a few. The body's response to mBI is significantly different as hemorrhaging and blood loss, tissue loss, hypoxia, significant neuron death etc. are not part of the manifestations of this condition.

Consequently, therapeutic treatments for each injury are significantly different. The same therapeutic methodology used for severe TBI, for example, surgery, deep sedation, mannitol therapy and operative decompression, would be contra-indicated for treatment of mBI, for example, concussion, which is a type of mild brain injury. The inverse, such as rest and mental relaxation with little intervention for recovering from mBI, is likewise true.

As used herein, the term "polypeptide" or "peptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, acylation, acylation by fatty acid, fatty acid-modification, derivatization by known protecting/blocking groups, proteolytic cleavage, or modification by non-naturally occurring amino acids. Modification may be fatty acid modification or triglyceride modification. Fatty acid modification may be a short to medium-chain fatty acid. The short fatty acid may be a two-carbon fatty acid or acetic acid. Medium chain fatty acid may be 14-carbon fatty acid or tetradecanoic acid. Modification with a fatty acid may be acylation of SEQ ID NO. 1 at serine amino acid position 2 and/or serine amino acid position 3. Modification may be catalyzed by ghrelin O-acyl transferase (GOAT) of fatty acid thioester and ghrelin as substrates. In one embodiment, post-translationally modified ghrelin may be bound and/or recognized by growth hormone secretagogue receptor type 1a (GHSR-1a) or ghrelin receptor. In one embodiment, post-translationally modified ghrelin may be fatty acid-acylated ghrelin at serine amino acid position 2 and/or serine amino acid position 3 bound and/or recognized by GHSR-1a or ghrelin receptor. A polypeptide may be derived from a natural biological source or produced by recombinant technology, but is not necessarily translated from a designated nucleic acid sequence. It may be generated in any manner, including by chemical synthesis. The term "Polypeptide" or "Peptide" also refers to a compound comprising a plurality of amino acids linked therein via peptide linkages. Here, the amino acid (also called an amino acid residue) includes naturally occurring amino acids represented by formula: $NH_2$—$CH(R')$—$COOH$, wherein R' is a naturally occurring substituent group, as well as its D, L-optical isomers etc. There is also a peptide, wherein a certain naturally occurring amino acid is replaced by a modified amino acid. The modified amino acid includes the amino acids of the above formula wherein the substituent group R' is further modified, its D, L-optical isomers thereof, and non-natural amino acids wherein e.g. various substituent groups are bound to the substituent group R' of the above formula via or not via an ester, ether, thioester, thioether, amide, carbamide or thiocarbamide linkage. The modified amino acid also includes non-natural amino acids whose amino groups are replaced by lower alkyl groups.

As used herein, the term "secretagogue" is a substance stimulating growth hormone release, such as ghrelin. In some embodiments, the ghrelin binds to the growth hormone secretagogue receptor GHS-R 1a (GHSR). The ghrelin compounds described herein are active at the receptor for growth hormone secretagogue (GHS), e.g., the receptor GHS-R 1a. The compounds can bind to GHS-R 1a, and stimulate receptor activity. In some embodiments, the compounds can bind other receptors and, optionally, stimulate their activity. In some embodiments, ghrelin increases uncoupling protein-2 (UCP-2) expression. In some embodiments, ghrelin increases UCP-2 expression in mitochondria. In some embodiments, ghrelin prevents the metabolic consequence of mBI and any associated chronic conditions.

Treatment of Mild Brain Injury (mBI) and other Neurological Disorders

The present disclosure is directed to the identification of a novel use for ghrelin in mBI. Mild BI, including concussion, has a significantly different pathology than other traumas associated with brain disease and illness and severe traumatic brain injuries (severe TBI) such as those causing ischemia. Mild BI does not cause the massive tissue and cellular damage as observed in severe traumatic brain disease. Rather mBI causes subtle metabolic changes within the brain, specifically oxidative stress and overproduction of reactive oxygen species (ROS) which, in turn, can damage neuroconnectivity and lead to neuron damage and encephalopathic and psychological changes with recurrent injury.

The present disclosure utilizes ghrelin in treating mBI. Unlike severe traumatic injury to the brain, mBI does not show acute neuronal histological changes, severe neuronal inflammation or significant cellular or vasogenic edema (i.e., blood brain barrier breakdown). Rather, mBI is a clinical condition generally associated with a list of clinical symptoms. It sometimes is associated with loss of consciousness but does not necessarily show significant radiological changes. Symptoms that often are reported include, without limitation, headache, "pressure in head," neck pain, nausea or vomiting, dizziness, blurred vision, balance problems, sensitivity to light, sensitivity to noise, feeling slowed down, feeling like "in a fog," "don't feel right," difficulty concentrating, difficulty remembering, fatigue or low energy, confusion, drowsiness, trouble falling asleep, more emotional, irritability, sadness and being nervous or anxious. In some non-limiting embodiments the methods herein can include or relate to treating or reducing one or more of the above listed symptoms. Most importantly, repeated concussions, as observed in the military and in sports such as football and hockey, cause a series of metabolic disturbances and the formation of ROS. These series of events lead to chronic traumatic encephalopathy (CTE) as witnessed in the autopsies of several deceased professional football players.

In some embodiments, ghrelin has the ability to decrease ROS and the subsequent damage caused to neurons following mBI. This is especially important for chronic concussions where preventing the inflammatory, excitatory milieu of ROS would have significant clinical impact. Ghrelin treatments decrease ROS, and therefore prevent the metabolic consequence of concussions and the chronic conditions that are associated thereof.

In some embodiments, the therapeutic effect of ghrelin in mBI is compared to its therapeutic effect in severe TBI. The etiology, imaging, and assessment of mBI lack a cohesive explanation for the observed cognitive deficits of chronic headaches, memory loss and sleep impairment. Only the most advanced and cumbersome technology can even detect subtle changes associated with mBI. Therefore, unlike severe TBI, where a definitive mass lesion is identified with anatomic and cellular changes, mBI is undetectable radiologically, nevertheless, specific metabolic derangements occur. The present disclosure describes that ghrelin can be potent neuro-conservative agents in mBI.

Without being limited by any theory, the present disclosure also describes the biological function of ghrelin following mBI. After mBI, the metabolic needs of the cell, including glucose requirements, increase. Mild injured cells have significant metabolic derangements causing reactive oxygen species on neurons. This metabolic stress and increased metabolic needs is the fundamental concept underlying acute concussion management. Decreasing ROS and improving glucose uptake of the brain or neuronal cells and axons can restore intracellular function and remain viable. This prevents or reduces concussion-induced dysfunction and overall improves neurocognitive outcome, as well as prevents memory loss, and chronic mBI states of headaches and development of chronic traumatic encephalopathy.

The present disclosure provides for a method of treating mild brain injury (mild BI or mBI) in a subject, comprising administering to the subject (e.g., a subject that has a mBI) an effective amount of a compound comprising ghrelin, thereby treating the mBI. The ghrelin can be administered for the purpose of treating the mBI in a therapeutically effective amount for the mBI. In some embodiments, the methods can further include selecting or identifying a subject that has suffered, is at risk of suffering, is prone to suffer, and/or is about to participate in an activity with a high risk for suffering, a mBI, prior to administration of the ghrelin.

In some embodiments, the mild brain injury comprises a concussion. In some embodiments, the subject that undergoes the method of treatment is a mammal. In some embodiments, the subject is a human, monkey, cow, goat, sheep, mouse, rat, cat, dog, horse, hamster, pig, fish and chicken. In some embodiments, ghrelin is administered within about 72 hours of the mBI. In some embodiments, ghrelin is administered within about 24 hours of the mBI. In some embodiments, ghrelin is administered at about 0.1, 0.3, 0.5, 0.7, 1, 2, 3, 6, 12, 18, 24, 36, 48, or 72 hours after the mBI.

The present disclosure also provides a method of treating mild brain injury (mBI) in a subject, comprising administering to the subject a therapeutically effective amount of ghrelin, thereby treating the mBI, wherein the ghrelin is the sole active agent. In some embodiments, the ghrelin has the sequence of Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg (SEQ ID NO. 1). In some embodiments, the ghrelin is modified with one or more fatty acids. In some embodiments, the fatty acid is an octanoic acid. In some embodiments, the ghrelin is modified at serine at amino acid position 2 and/or serine at amino acid position 3 of SEQ ID NO. 1. In some embodiments, the ghrelin is modified at serine at amino acid position 2 and/or serine amino acid position 3 with an octanoic acid. In some embodiments, modification of ghrelin is acylation of ghrelin at serine at amino acid position 2 and/or serine at amino acid position 3 with an octanoic acid. In some embodiments, the ghrelin so modified is an octanoyl-ghrelin with an acylation at serine at amino acid position 3 by the octanoic acid. In some embodiments, the mBI comprises a concussion. In some embodiments, the subject is a mammal. In some embodiments, ghrelin is administered, at least for a first administration (but not limited to), within or in less than about 24 hours, or less than 48 hours, or less than 72 hours of the mBI, or any sub value or subrange between immediately after the injury and those time periods. In some embodiments, ghrelin is administered within not more than about 8 hours of the mBI. In some embodiments the ghrelin can be administered with about 6 hours of the mBI. In some embodiments, the ghrelin can be administered a single dose, or in multiple doses, for example 2-3 doses. The multiple doses can have at least a first dose administered with the time period mentioned herein and one or more subsequent doses after the time period. In some embodiments, the ghrelin is administered in an amount that results in ghrelin blood levels being at least 1, at least 1.5, at least two times (or more) greater than the endogenous ghrelin blood levels of the subject. In some embodiments, ghrelin is administered in a single dose. In some embodiments, ghrelin is administered at a dosage from 10 ng/kg per day to 10 mg/kg per day or per dose. In some embodiments, the dosage of ghrelin can be between 1 microgram and 15 micrograms per kg, for example about 10 μg/kg. In some embodiments, ghrelin is administered at a dosage of 2 μg/kg per dose or in some case per day. In some embodiments, the ghrelin has a carbon 14 (C14) content of less than 1 part per trillion (ppt).

The present disclosure also provides a method of treating mild brain injury (mBI) in a subject, comprising administering to the subject a therapeutically effective amount of ghrelin in an amount that provides blood levels of ghrelin that are at least 1.5 times greater than endogenous ghrelin blood levels of the subject, thereby treating the mBI. The ghrelin can be the sole active agent. In some embodiments, the ghrelin has the sequence of Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg (SEQ ID NO. 1). In some embodiments, the ghrelin is modified with one or more fatty acids. In some embodiments, the fatty acid is an octanoic acid. In some embodiments, the ghrelin is modified at serine at amino acid position 2 and/or serine at amino acid position 3 of SEQ ID NO. 1. In some embodiments, the ghrelin is modified at serine at amino acid position 2 and/or serine at amino acid position 3 with an octanoic acid. In some embodiments, modification of ghrelin is acylation of ghrelin at serine at amino acid position 2 and/or serine at amino acid position 3 with an octanoic acid. In some embodiments, the ghrelin so modified is an octanoyl-ghrelin with an acylation at serine at amino acid position 3 by the octanoic acid. In some embodiments, the mBI comprises a concussion. In some embodiments, ghrelin is administered in a single dose. In some embodiments, the amount administered provides a blood level of at least 1.0 to 100 times greater the amount found endogenously in the subject. In some embodiments, the amount administered results in a blood level of at least 55 picograms/mL. In some embodiments, ghrelin is administered at a dosage from 10 ng/kg per day to 10 mg/kg per dosage and/or per day. In some embodiments, the dosage of ghrelin can be between 1 microgram and 15 micrograms per kg, for example about 10 μg/kg. In some embodiments, ghrelin is administered at a dosage of 2 μg/kg per dose or in some case per day. In some embodiments, the ghrelin has a carbon 14 (C14) content of less than 1 part per trillion (ppt). In some embodiments, the ghrelin is administered in an amount that provides blood levels of ghrelin that are at least 1.0, 2.0 times, or more, greater than endogenous ghrelin blood levels of the subject, thereby treating the mBI.

The present disclosure provides a method of treating mild brain injury (mBI) in a subject, comprising administering to the subject a therapeutically effective amount of a pharmaceutical composition consisting essentially of ghrelin. In some embodiment, ghrelin is the sole active agent. In some embodiments, the ghrelin is administered to the subject in an amount that provides blood levels of ghrelin that are at least 1.0, 1.5, 2.0 or more times greater than endogenous ghrelin blood levels of the subject, thereby treating the mBI. In some embodiments, the ghrelin is administered in an amount that provides blood levels of ghrelin that are at least 2.0 times greater than endogenous ghrelin blood levels of the subject, thereby treating the mBI.

In some embodiments, the subject is free of intracranial hypertension. In some embodiments, the subject is free of blood brain barrier vascular permeability. In some embodiments, the subject is free of necrosis of brain tissue. In some embodiment, the subject is free of massive brain tissue or cellular damage associated with brain injury. In some embodiment, the subject is free of severe neuronal inflammation or significant cellular or vasogenic edema in the subject's head. In some embodiments, the subject is free of injury-associated gross anatomical changes to the subject's brain.

In some embodiments, the subject is free of intracranial hypertension, blood brain barrier vascular permeability, or necrosis of brain tissue. In some embodiments, the subject is free of massive brain tissue or cellular damage associated with brain injury, severe neuronal inflammation or significant cellular or vasogenic edema in the subject's head, or injury-associated gross anatomical changes to the subject's brain.

In some embodiments, the subject is free of intracranial hypertension, blood brain barrier vascular permeability, necrosis of brain tissue, massive brain tissue or cellular damage associated with brain injury, severe neuronal inflammation or significant cellular or vasogenic edema in the subject's head, or injury-associated gross anatomical changes to the subject's brain. In some embodiments, the subject is free of intracranial hypertension, blood brain barrier vascular permeability, necrosis of brain tissue, massive brain tissue or cellular damage associated with brain injury, severe neuronal inflammation or significant cellular or vasogenic edema in the subject's head, and injury-associated gross anatomical changes to the subject's brain or combinations thereof.

In some embodiments, mBI is associated with loss of cognitive or motor skills. In some embodiments, mBI is associated metabolic derangements. In some embodiments, mBI is associated with chronic traumatic encephalopathy (CTE). In some embodiments, mBI is associated with neuroconnectivity damage. In some embodiments, mBI is associated with encephalopathic and/or psychological changes. In some embodiments, mBI is associated with loss of consciousness.

In some embodiments, mBI is associated with loss of cognitive or motor skills and metabolic derangements. In some embodiment, mBI is associated with chronic traumatic encephalopathy (CTE) and neuroconnectivity damage. In some embodiments, mBI is associated with psychological changes and loss of consciousness. In some embodiments, mBI is associated with loss of cognitive or motor skills, metabolic derangements, chronic traumatic encephalopathy (CTE), neuroconnectivity damage, psychological changes, or loss of consciousness. In some embodiments, mBI is associated with loss of cognitive or motor skills, metabolic derangements, chronic traumatic encephalopathy (CTE), neuroconnectivity damage, psychological changes, and loss of consciousness or combination thereof.

The present invention provides a method for reducing, inhibiting and/or minimizing damage to neurons associated with oxidative stress and overproduction of reactive oxidative species (ROS) with one or more incidence of mild brain injury (mBI) or concussion in a subject, comprising administering to the subject a therapeutically effective amount of ghrelin, wherein the ghrelin so administered reduces oxidative stress and overproduction of ROS, thereby inhibiting damage to neurons associated with oxidative stress and overproduction of reactive oxidative species (ROS) with one or more incidence of the mBI or concussion in the subject. In one embodiment, the ghrelin has a carbon 14 (C14) content of less than 1 part per trillion (ppt). In one embodiment, the ghrelin is the sole active agent. In one embodiment, the ghrelin has a carbon 14 (C14) content of less than 1 part per trillion (ppt) and ghrelin is the sole active agent.

The present invention further provides a method for inhibiting damage to neurons associated with oxidative stress and overproduction of reactive oxidative species (ROS) with one or more incidence of mild brain injury (mBI), including concussion, in a subject, comprising administering to the subject a therapeutically effective amount of ghrelin, wherein the ghrelin so administered reduces oxidative stress and overproduction of ROS and wherein the ghrelin is the sole active agent, thereby inhibiting damage to neurons associated with oxidative stress and overproduction of reactive oxidative species (ROS) with one or more incidence of the mBI or concussion in the subject.

The present invention additionally provides a method for inhibiting damage to neurons associated with oxidative stress and overproduction of reactive oxidative species (ROS) with one or more incidence of mild brain injury (mBI) or concussion in a subject, comprising administering to the subject a therapeutically effective amount of ghrelin having a carbon 14 (C14) content of less than 1 part per trillion (ppt), wherein the ghrelin so administered reduces oxidative stress and overproduction of ROS, thereby inhibiting damage to neurons associated with oxidative stress and overproduction of reactive oxidative species (ROS) with one or more incidence of the mBI or concussion in the subject.

The present invention also provides a method for inhibiting damage to neurons associated with oxidative stress and overproduction of reactive oxidative species (ROS) with one or more incidence of mild brain injury (mBI) or concussion in a subject, comprising administering to the subject a therapeutically effective amount of ghrelin having a carbon 14 (C14) content of less than 1 part per trillion (ppt), wherein the ghrelin so administered reduces oxidative stress and overproduction of ROS and wherein the ghrelin is the sole active agent, thereby inhibiting damage to neurons associated with oxidative stress and overproduction of reactive oxidative species (ROS) with one or more incidence of the mBI or concussion in the subject Additionally, the present invention discloses a method of restoring intracellular function after mild brain injury (mBI) in a subject, comprising administering to the subject a therapeutically effective amount of ghrelin so as to decrease ROS and improve glucose uptake of brain or neuronal cells and axons, thereby restoring intracellular function after mBI in the subject. In one embodiment, the ghrelin has a carbon 14 (C14) content of less than 1 part per trillion (ppt). In one embodiment, the ghrelin is the sole active agent. In one embodiment, the ghrelin has a carbon 14 (C14) content of less than 1 part per trillion (ppt) and is the sole active agent.

The present invention further provides a method of restoring intracellular function after mild brain injury (mBI) in a subject, comprising administering to the subject a therapeutically effective amount of ghrelin so as to decrease ROS and improve glucose uptake of brain or neuronal cells and axons, wherein the ghrelin is the sole active agent, thereby restoring intracellular function after mBI in the subject.

The present invention further still provides a method of restoring intracellular function after mild brain injury (mBI) in a subject, comprising administering to the subject a therapeutically effective amount of ghrelin having a carbon 14 (C14) content of less than 1 part per trillion (ppt) so as to decrease ROS and improve glucose uptake of brain or neuronal cells and axons, thereby restoring intracellular function after mBI in the subject.

The present invention also provides a method of restoring intracellular function after mild brain injury (mBI) in a subject, comprising administering to the subject a therapeutically effective amount of ghrelin having a carbon 14 (C14) content of less than 1 part per trillion (ppt) so as to decrease ROS and improve glucose uptake of brain or neuronal cells and axons, wherein the ghrelin is the sole active agent, thereby restoring intracellular function after mBI in the subject.

Further, the present invention provides a method of treating mild brain injury (mBI) in a subject free of brain edema, intracranial hypertension, blood brain barrier vascular permeability, necrosis, or massive tissue or cellular damage associated with brain injury, comprising administering to the subject a therapeutically effective amount of ghrelin, thereby treating the mBI. In one embodiment, the ghrelin has a carbon 14 (C14) content of less than 1 part per trillion (ppt). In one embodiment, the ghrelin is the sole active agent. In one embodiment, the ghrelin has a carbon 14 (C14) content of less than 1 part per trillion (ppt) and is the sole active agent.

The present invention additionally provides a method of treating mild brain injury (mBI) in a subject free of brain edema, intracranial hypertension, blood brain barrier vascular permeability, necrosis, or massive tissue or cellular damage associated with brain injury, comprising administering to the subject a therapeutically effective amount of ghrelin, wherein the ghrelin is the sole active agent, thereby treating the mBI. The present invention discloses a method of treating mild brain injury (mBI) in a subject free of brain edema, intracranial hypertension, blood brain barrier vascular permeability, necrosis, or massive tissue or cellular damage associated with brain injury, comprising administering to the subject a therapeutically effective amount of ghrelin having a carbon 14 (C14) content of less than 1 part per trillion (ppt), thereby treating the mBI.

The present invention yet also provides a method of treating mild brain injury (mBI) in a subject free of brain edema, intracranial hypertension, blood brain barrier vascular permeability, necrosis, or massive tissue or cellular damage associated with brain injury, comprising administering to the subject a therapeutically effective amount of ghrelin having a carbon 14 (C14) content of less than 1 part per trillion (ppt), wherein the ghrelin is the sole active agent, thereby treating the mBI.

Also, the present invention provides a method of treating mild brain injury (mBI) in a subject free of brain edema, intracranial hypertension, blood brain barrier vascular permeability, necrosis or massive tissue and cellular damage associated with brain injury, comprising administering to the subject a therapeutically effective amount of ghrelin in an amount that provides blood levels of ghrelin that are at least 1.5 times greater than endogenous ghrelin blood levels of the subject, thereby treating the mBI. In one embodiment, the ghrelin has a carbon 14 (C14) content of less than 1 part per trillion (ppt). In one embodiment, the ghrelin is the sole active agent. In one embodiment, the ghrelin has a carbon 14 (C14) content of less than 1 part per trillion (ppt) and is the sole active agent.

The present invention provides a method of treating mild brain injury (mBI) in a subject free of brain edema, intracranial hypertension, blood brain barrier vascular permeability, necrosis or massive tissue and cellular damage associated with brain injury, comprising administering to the subject a therapeutically effective amount of ghrelin in an amount that provides blood levels of ghrelin that are at least 1.5 times greater than endogenous ghrelin blood levels of the subject, wherein the ghrelin is the sole active agent, thereby treating the mBI.

The present invention yet further provides a method of treating mild brain injury (mBI) in a subject free of brain edema, intracranial hypertension, blood brain barrier vascular permeability, necrosis or massive tissue and cellular damage associated with brain injury, comprising administering to the subject a therapeutically effective amount of ghrelin having a carbon 14 (C14) content of less than 1 part per trillion (ppt) and in an amount that provides blood levels of ghrelin that are at least 1.5 times greater than endogenous ghrelin blood levels of the subject, thereby treating the mBI.

The present invention also provides a method of treating mild brain injury (mBI) in a subject free of brain edema, intracranial hypertension, blood brain barrier vascular permeability, necrosis or massive tissue and cellular damage associated with brain injury, comprising administering to the subject a therapeutically effective amount of ghrelin having a carbon 14 (C14) content of less than 1 part per trillion (ppt) and in an amount that provides blood levels of ghrelin that are at least 1.5 times greater than endogenous ghrelin blood levels of the subject, wherein the ghrelin is the sole active agent, thereby treating the mBI.

The present invention further provides a method of treating metabolic derangements associated with mild brain injury (mBI) or concussion in a subject, comprising administering to the subject a therapeutically effective amount of ghrelin, thereby treating metabolic derangements associated with mBI or concussion in the subject. In one embodiment, the ghrelin has a carbon 14 (C14) content of less than 1 part per trillion (ppt). In one embodiment, the ghrelin is the sole active agent. In one embodiment, the ghrelin has a carbon 14 (C14) content of less than 1 part per trillion (ppt) and is the sole active agent.

The present invention discloses a method of treating metabolic derangements associated with mild brain injury (mBI) or concussion in a subject, comprising administering to the subject a therapeutically effective amount of ghrelin, wherein the ghrelin is the sole active agent, thereby treating metabolic derangements associated with mBI or concussion in the subject.

The present invention provides a method of treating metabolic derangements associated with mild brain injury (mBI) or concussion in a subject, comprising administering to the subject a therapeutically effective amount of ghrelin having a carbon 14 (C14) content of less than 1 part per trillion (ppt), thereby treating metabolic derangements associated with mBI or concussion in the subject.

The present invention further still provides a method of treating metabolic derangements associated with mild brain injury (mBI) or concussion in a subject, comprising administering to the subject a therapeutically effective amount of ghrelin having a carbon 14 (C14) content of less than 1 part per trillion (ppt), wherein the ghrelin is the sole active agent, thereby treating metabolic derangements associated with mBI or concussion in the subject.

The present invention provides a method of treating metabolic derangements associated with mild brain injury (mBI) or concussion in a subject, comprising administering to the subject a therapeutically effective amount of ghrelin in an amount that provides blood levels of ghrelin that are at least 1.5 times greater than endogenous ghrelin blood levels of the subject, thereby treating metabolic derangements associated with mBI or concussion in the subject. In one embodiment, the ghrelin has a carbon 14 (C14) content of less than 1 part per trillion (ppt). In one embodiment, the ghrelin is the sole active agent. In one embodiment, the ghrelin has a carbon 14 (C14) content of less than 1 part per trillion (ppt) and is the sole active agent.

The present invention provides a method of treating metabolic derangements associated with mild brain injury (mBI) or concussion in a subject, comprising administering to the subject a therapeutically effective amount of ghrelin in an amount that provides blood levels of ghrelin that are at least 1.5 times greater than endogenous ghrelin blood levels of the subject, wherein the ghrelin is the sole active agent, thereby treating metabolic derangements associated with mBI or concussion in the subject.

The present invention provides a method of treating metabolic derangements associated with mild brain injury (mBI) or concussion in a subject, comprising administering to the subject a therapeutically effective amount of ghrelin in an amount that provides blood levels of ghrelin that are at least 1.5 times greater than endogenous ghrelin blood levels of the subject, wherein the ghrelin has a carbon 14 (C14) content of less than 1 part per trillion (ppt), thereby treating metabolic derangements associated with mBI or concussion in the subject.

The present invention provides a method of treating metabolic derangements associated with mild brain injury (mBI) or concussion in a subject, comprising administering to the subject a therapeutically effective amount of ghrelin in an amount that provides blood levels of ghrelin that are at least 1.5 times greater than endogenous ghrelin blood levels of the subject, wherein the ghrelin has a carbon 14 (C14) content of less than 1 part per trillion (ppt) and is the sole active agent, thereby treating metabolic derangements associated with mBI or concussion in the subject.

The present invention provides a method for preventing damage to neurons associated with oxidative stress and overproduction of reactive oxidative species (ROS) with one or more incidence of mild brain injury (mBI) or concussion in a subject, comprising administering to the subject a therapeutically effective amount of ghrelin, wherein ghrelin treatment reduces oxidative stress and overproduction of ROS, thereby preventing damage to neurons associated with oxidative stress and overproduction of reactive oxidative species (ROS) with one or more incidence of the mBI or concussion in the subject. In one embodiment, the ghrelin has a carbon 14 (C14) content of less than 1 part per trillion (ppt). In one embodiment, the ghrelin is the sole active agent. In one embodiment, the ghrelin has a carbon 14 (C14) content of less than 1 part per trillion (ppt) and is the sole active agent. The present invention discloses a method for preventing damage to neurons associated with oxidative stress and overproduction of reactive oxidative species (ROS) with one or more incidence of mild brain injury (mBI) or concussion in a subject, comprising administering to the subject a therapeutically effective amount of ghrelin, wherein ghrelin treatment reduces oxidative stress and overproduction of ROS and wherein the ghrelin is the sole active agent, thereby preventing damage to neurons associated with oxidative stress and overproduction of reactive oxidative species (ROS) with one or more incidence of the mBI or concussion in the subject.

The present invention provides a method for preventing damage to neurons associated with oxidative stress and overproduction of reactive oxidative species (ROS) with one or more incidence of mild brain injury (mBI) or concussion in a subject, comprising administering to the subject a therapeutically effective amount of ghrelin having a carbon 14 (C14) content of less than 1 part per trillion (ppt), wherein ghrelin treatment reduces oxidative stress and overproduction of ROS, thereby preventing damage to neurons associated with oxidative stress and overproduction of reactive oxidative species (ROS) with one or more incidence of the mBI or concussion in the subject.

The present invention provides a method for preventing damage to neurons associated with oxidative stress and overproduction of reactive oxidative species (ROS) with one or more incidence of mild brain injury (mBI) or concussion in a subject, comprising administering to the subject a therapeutically effective amount of ghrelin having a carbon 14 (C14) content of less than 1 part per trillion (ppt), wherein ghrelin treatment reduces oxidative stress and overproduction of ROS and wherein the ghrelin is the sole active agent, thereby preventing damage to neurons associated with oxidative stress and overproduction of reactive oxidative species (ROS) with one or more incidence of the mBI or concussion in the subject.

The present invention provides a method for preventing damage to neurons associated with oxidative stress and overproduction of reactive oxidative species (ROS) with one or more incidence of mild brain injury (mBI) or concussion in a subject, comprising administering to the subject a therapeutically effective amount of ghrelin in an amount that provides blood levels of ghrelin that are at least 1.5 times greater than endogenous ghrelin blood levels of the subject, wherein ghrelin treatment reduces oxidative stress and overproduction of ROS, thereby preventing damage to neurons associated with oxidative stress and overproduction of reactive oxidative species (ROS) with one or more incidence of the mBI or concussion in the subject. In one embodiment, the ghrelin has a carbon 14 (C14) content of less than 1 part per trillion (ppt). In one embodiment, the ghrelin is the sole active agent. In one embodiment, the ghrelin has a carbon 14 (C14) content of less than 1 part per trillion (ppt) and is the sole active agent.

The present invention provides a method for preventing damage to neurons associated with oxidative stress and overproduction of reactive oxidative species (ROS) with one or more incidence of mild brain injury (mBI) or concussion in a subject, comprising administering to the subject a therapeutically effective amount of ghrelin in an amount that provides blood levels of ghrelin that are at least 1.5 times greater than endogenous ghrelin blood levels of the subject, wherein ghrelin treatment reduces oxidative stress and overproduction of ROS and wherein the ghrelin is the sole active agent, thereby preventing damage to neurons associated with oxidative stress and overproduction of reactive oxidative species (ROS) with one or more incidence of the mBI or concussion in the subject.

The present invention provides a method for preventing damage to neurons associated with oxidative stress and overproduction of reactive oxidative species (ROS) with one or more incidence of mild brain injury (mBI) or concussion in a subject, comprising administering to the subject a therapeutically effective amount of ghrelin in an amount that provides blood levels of ghrelin that are at least 1.5 times greater than endogenous ghrelin blood levels of the subject, wherein ghrelin treatment reduces oxidative stress and overproduction of ROS and wherein the ghrelin has a carbon 14 (C14) content of less than 1 part per trillion (ppt), thereby preventing damage to neurons associated with oxidative stress and overproduction of reactive oxidative species (ROS) with one or more incidence of the mBI or concussion in the subject.

The present invention provides a method for reducing damage to neurons associated with oxidative stress and overproduction of reactive oxidative species (ROS) with one or more incidence of mild brain injury (mBI) or concussion in a subject, comprising administering to the subject a therapeutically effective amount of ghrelin in an amount that provides blood levels of ghrelin that are at least 1.5 times greater than endogenous ghrelin blood levels of the subject, wherein ghrelin treatment reduces oxidative stress and overproduction of ROS and wherein the ghrelin has a carbon 14 (C14) content of less than 1 part per trillion (ppt) and is the sole active agent, thereby preventing damage to neurons associated with oxidative stress and overproduction of reactive oxidative species (ROS) with one or more incidence of the mBI or concussion in the subject.

The present invention provides a method of treating mild brain injury (mBI) in a subject, free of acute neuronal histological changes, severe neuronal inflammation or significant cellular or vasogenic edema, comprising administering to the subject a therapeutically effective amount of ghrelin, thereby treating the mBI in the subject free of acute neuronal histological changes, severe neuronal inflammation or significant cellular or vasogenic edema. In one embodiment, the ghrelin has a carbon 14 (C14) content of less than 1 part per trillion (ppt). In one embodiment, the ghrelin is the sole active agent. In one embodiment, the ghrelin has a carbon 14 (C14) content of less than 1 part per trillion (ppt) and is the sole active agent.

The present invention provides a method of treating mild brain injury (mBI) in a subject, free of acute neuronal histological changes, severe neuronal inflammation or significant cellular or vasogenic edema, comprising administering to the subject a therapeutically effective amount of ghrelin, wherein the ghrelin is the sole active agent, thereby treating the mBI in the subject free of acute neuronal histological changes, severe neuronal inflammation or significant cellular or vasogenic edema.

The present invention provides a method of treating mild brain injury (mBI) in a subject, free of acute neuronal histological changes, severe neuronal inflammation or significant cellular or vasogenic edema, comprising administering to the subject a therapeutically effective amount of ghrelin having a carbon 14 (C14) content of less than 1 part per trillion (ppt), thereby treating the mBI in the subject free of acute neuronal histological changes, severe neuronal inflammation or significant cellular or vasogenic edema.

The present invention provides a method of treating mild brain injury (mBI) in a subject, free of acute neuronal histological changes, severe neuronal inflammation or significant cellular or vasogenic edema, comprising administering to the subject a therapeutically effective amount of ghrelin having a carbon 14 (C14) content of less than 1 part per trillion (ppt), wherein the ghrelin is the sole active agent, thereby treating the mBI in the subject free of acute neuronal histological changes, severe neuronal inflammation or significant cellular or vasogenic edema.

The present invention provides a method of treating mild brain injury (mBI) in a subject, comprising administering to the subject, free of acute neuronal histological changes, severe neuronal inflammation or significant cellular or vasogenic edema, a therapeutically effective amount of ghrelin in an amount that provides blood levels of ghrelin that are at least 1.5 times greater than endogenous ghrelin blood levels of the subject, thereby treating the mBI in the subject free of acute neuronal histological changes, severe neuronal inflammation or significant cellular or vasogenic edema. In one embodiment, the ghrelin has a carbon 14 (C14) content of less than 1 part per trillion (ppt). In one embodiment, the ghrelin is the sole active agent. In one embodiment, the ghrelin has a carbon 14 (C14) content of less than 1 part per trillion (ppt) and is the sole active agent.

The present invention provides a method of treating mild brain injury (mBI) in a subject, comprising administering to the subject, free of acute neuronal histological changes, severe neuronal inflammation or significant cellular or vasogenic edema, a therapeutically effective amount of ghrelin in an amount that provides blood levels of ghrelin that are at least 1.5 times greater than endogenous ghrelin blood levels of the subject, wherein the ghrelin is the sole active agent, thereby treating the mBI in the subject free of acute neuronal histological changes, severe neuronal inflammation or significant cellular or vasogenic edema.

The present invention provides a method of treating mild brain injury (mBI) in a subject, comprising administering to the subject, free of acute neuronal histological changes, severe neuronal inflammation or significant cellular or vasogenic edema, a therapeutically effective amount of ghrelin in an amount that provides blood levels of ghrelin that are at least 1.5 times greater than endogenous ghrelin blood levels of the subject, wherein the ghrelin has a carbon 14 (C14) content of less than 1 part per trillion (ppt), thereby treating the mBI in the subject free of acute neuronal histological changes, severe neuronal inflammation or significant cellular or vasogenic edema.

The present invention provides a method of treating mild brain injury (mBI) in a subject, comprising administering to the subject, free of acute neuronal histological changes, severe neuronal inflammation or significant cellular or vasogenic edema, a therapeutically effective amount of ghrelin in an amount that provides blood levels of ghrelin that are at least 1.5 times greater than endogenous ghrelin blood levels of the subject, wherein the ghrelin the ghrelin has a carbon 14 (C14) content of less than 1 part per trillion (ppt) and is the sole active agent, thereby treating the mBI in the subject free of acute neuronal histological changes, severe neuronal inflammation or significant cellular or vasogenic edema.

The present invention provides a method of treating or reducing symptoms of mild brain injury (mBI) in a subject, comprising administering to the subject a therapeutically effective amount of ghrelin, thereby treating or reducing symptoms of the mBI. In one embodiment, the ghrelin has a carbon 14 (C14) content of less than 1 part per trillion (ppt). In one embodiment, the ghrelin is the sole active agent. In one embodiment, the ghrelin has a carbon 14 (C14) content of less than 1 part per trillion (ppt) and is the sole active agent.

The present invention provides a method of treating or reducing symptoms of mild brain injury (mBI) in a subject, comprising administering to the subject a therapeutically effective amount of ghrelin, wherein the ghrelin is the sole active agent, thereby treating or reducing symptoms of the mBI.

The present invention provides a method of treating or reducing symptoms of mild brain injury (mBI) in a subject, comprising administering to the subject a therapeutically effective amount of ghrelin having a carbon 14 (C14) content of less than 1 part per trillion (ppt), thereby treating or reducing symptoms of the mBI.

The present invention provides a method of treating or reducing symptoms of mild brain injury (mBI) in a subject, comprising administering to the subject a therapeutically effective amount of ghrelin having a carbon 14 (C14) content of less than 1 part per trillion (ppt), wherein the ghrelin is the sole active agent, thereby treating or reducing symptoms of the mBI.

The present invention provides a method of treating or reducing symptoms of mild brain injury (mBI) in a subject, comprising administering to the subject a therapeutically effective amount of ghrelin in an amount that provides blood levels of ghrelin that are at least 1.5 times greater than endogenous ghrelin blood levels of the subject, thereby treating or reducing symptoms of the mBI. In one embodiment, the ghrelin has a carbon 14 (C14) content of less than 1 part per trillion (ppt). In one embodiment, the ghrelin is the sole active agent. In one embodiment, the ghrelin has a carbon 14 (C14) content of less than 1 part per trillion (ppt) and is the sole active agent.

The present invention provides a method of treating or reducing symptoms of mild brain injury (mBI) in a subject, comprising administering to the subject a therapeutically effective amount of ghrelin in an amount that provides blood levels of ghrelin that are at least 1.5 times greater than endogenous ghrelin blood levels of the subject, wherein the ghrelin is the sole active agent, thereby treating or reducing symptoms of the mBI.

The present invention provides a method of treating or reducing symptoms of mild brain injury (mBI) in a subject, comprising administering to the subject a therapeutically effective amount of ghrelin in an amount that provides blood levels of ghrelin that are at least 1.5 times greater than endogenous ghrelin blood levels of the subject, wherein the ghrelin has a carbon 14 (C14) content of less than 1 part per trillion (ppt), thereby treating or reducing symptoms of the mBI.

The present invention provides a method of treating or reducing symptoms of mild brain injury (mBI) in a subject, comprising administering to the subject a therapeutically effective amount of ghrelin in an amount that provides blood levels of ghrelin that are at least 1.5 times greater than endogenous ghrelin blood levels of the subject, wherein the ghrelin has a carbon 14 (C14) content of less than 1 part per trillion (ppt) and is the sole active agent, thereby treating or reducing symptoms of the mBI.

In some embodiments, the symptoms of mBI are any of headache, "pressure in head," neck pain, nausea or vomiting, dizziness, blurred vision, balance problems, sensitivity to light, sensitivity to noise, feeling slowed down, feeling like "in a fog," "don't feel right," difficulty concentrating, difficulty remembering, fatigue or low energy, confusion, drowsiness, loss of consciousness, trouble falling asleep, more emotional, irritability, sadness and being nervous or anxious.

As discussed herein, ghrelin can be used to treat and/or reduce the severity of mild brain injuries, such as for example, concussions. The ghrelin can be provided or administered as described herein. As described elsewhere herein, ghrelin can be the sole active agent administered to a subject. For example, ghrelin can be the only active ingredient for treating the mBI or reducing the severity of the mBI. In some embodiments, additional active agents are specifically excluded. For example, in some of the methods herein where ghrelin is administered, the methods can specifically exclude the use or administration of other compounds, such as, for example, selective androgen receptor modulators, steroid receptor modulators, ligand for a glucocorticoid receptor, or a modulator of the NF-kB signaling pathway.

In the embodiments described herein it should be understood that mBI is different from and is not severe TBI.

In some embodiments, mBI or concussion is diagnosed by non-invasive functional imaging following impact. In some embodiments, mBI or concussion is diagnosed by neuropsychological assessment following impact. In some embodiment, mBI or concussion is diagnosed by neuroanatomical assessment of the brain following impact. In some embodiment, the neuroanatomical assessment of the brain following impact is at the cellular level or molecular level. In some embodiment, mBI or concussion is diagnosed by cognitive assessment following impact. In some embodiment, mBI or concussion is diagnosed by assessment of alertness following impact. In some embodiments, mBI and concussion can be diagnosed and/or assessed by evaluating one or more of consciousness, assessment of alertness, assessment of orientation, assessment of cognitive function, assessment of psychological state, neuropsychological assessment.

In some embodiments, mBI or concussion is diagnosed using a Glasgow Coma Scale (GCS) having a score of 13 to 15. In some embodiments, mBI or concussion is diagnosed using a Glasgow Coma Scale (GCS) having a score of 13 or greater.

In contrast, by way of example, severe TBI generally has a GCS score of 8 or below.

In some embodiments, an intravenous injection of ghrelin is employed. The administration route must ensure that the non-degraded, bioactive form of the peptide will be the dominating form in the circulation, which will reach and stimulate the ghrelin receptors in order to obtain the maximum effect of ghrelin treatment on mBI. In some embodiments, ghrelin is administered within about 30 minutes of the incident that results in mBI. In some embodiments, ghrelin is administered within about 30 minutes to about 2 hours of the incident that results in mBI. In some embodiments, ghrelin is administered within about 30 minutes to about 6 hours of the incident that results in mBI. In some embodiments, ghrelin is administered within about 30 minutes to about 12 hours of the incident that results in mBI.

A typical dosage is in a concentration equivalent to from 10 ng to 10 mg ghrelin per kg bodyweight. In some embodiments, ghrelin is administered in a concentration equivalent to from about 0.1 µg to about 1 mg ghrelin per kg bodyweight, such as from about 0.5 µg to about 0.5 mg ghrelin per kg bodyweight, such as from about 1.0 µg to about 0.1 mg ghrelin per kg bodyweight, such as from about 1.0 µg to about 50 µg ghrelin per kg bodyweight, such as from about 1.0 µg to about 10 µg ghrelin per kg bodyweight. In some embodiments, about 10 µg ghrelin powder is reconstituted in about 100 µL of a sterile saline solution before administration. In some embodiments, the sterile saline solution is contained in an IV bag for ease of delivery.

In some embodiments, the ghrelin and ghrelin or ghrelin agonist is used in an assay to assess the ability of candidate compounds to effect increased uncoupling protein-2 (UCP-2) expression including increased UCP-2 expression in mitochondria. In such assays, ghrelin is used as a control to determine the relative efficacy of the candidate compound or compounds. Suitable assays include by way of example only competitive assays for binding of a candidate compound or compounds to growth hormone secretagogue receptor 1a (i.e., GHSR-1a) in the presence of ghrelin as well as frontal affinity chromatography.

Any competitive binding assay known in the art is applicable for binding of a candidate compound or compounds to growth hormone secretagogue receptor in the presence of ghrelin, using either heterogeneous or homogeneous methods, with one or more reagents, and with labels and detection methods. By way of non-limiting example, detection methods may include radioactive methods; enzyme techniques using intact enzymes of many types including, for example, β-galactosidase, glucose 6-phosphate dehydrogenase, alkaline phosphatase, horseradish peroxidase, or glucose oxidase; techniques using enzyme fragments, such as β-galactosidase complementation assays; detection systems including chromogenic substrates; fluorescent methods detected by direct fluorescence, time-resolved fluorescence, fluorescence polarization, or fluorescence energy transfer; and chemical or bioluminescence detection systems.

In some embodiments, frontal affinity chromatography (FAC) can be used for screening of compound libraries. The basic premise of FAC is that continuous infusion of a compound will allow for equilibration of the ligand between the free and bound states, where the precise concentration of free ligand is known. The detection of compounds eluting from the column can be accomplished using methods such as fluorescence, radioactivity, or electrospray mass spectrometry. The former two methods usually make use of either a labeled library, or use a labeled indicator compound, which competes against known unlabeled compounds, getting displaced earlier if a stronger binding ligand is present.

In some embodiments, a patient suffering loss of cognitive or motor skills due to mBI and, in particular, repetitive mBI, can be monitored for therapy or progression of such skills by correlating the ghrelin level in the patient's brain over time. As the ghrelin levels decrease, there will be an increased need for intervention.

This invention also provides for methods for measuring ghrelin levels before starting a sport or activity, for example prior to the beginning of football season (or any other sport or activity, including those listed elsewhere herein), and monitoring ghrelin levels during the season to ascertain if the player or participant is at a level not qualified to play or participate. The methods can include the use of any suitable measurement or assay technique for measuring ghrelin levels, such as from blood to determine if blood levels correlate to brain levels.

With the benefit of the instant embodiments, the skilled artisan can select any suitable technique for measuring ghrelin levels. A number of assays known in the art for measuring a protein or hormone level are applicable for measuring ghrelin levels. By way of non-limiting example, assays such as a blood sugar test by extracting a drop of blood and putting it into a device, can quantitatively assess the amount of ghrelin, or an assay involving measuring a range of substances whereby a specific reaction chemistry is followed photo-metrically with time, for example by utilizing an antibody specific to ghrelin that is coated onto latex particles and measuring the increased turbidity that is produced when ghrelin being measured promotes aggregation of the latex particles as the reaction between ghrelin and anti-ghrelin antibody proceeds. This measurement of increasing turbidity can be achieved using a conventional photometer and using the associated scientific principles of photometric measurements. Such concentration dependent turbidity is then compared to that produced by standards which are established in the art.

Further compatible, but non-limiting, methodologies include carrying out a series of enzyme-linked reactions in solution, where ghrelin in the plasma fraction of a whole blood sample is altered by an enzyme-promoted reaction to ultimately derive a colored dye from colorless reaction constituents. The color is developed in a time dependent way and monitored photo-metrically. This measurement of color change can also be achieved using a conventional photometer using the associated scientific principles of photometric measurements. Such concentration dependent change in transmission is then compared to that produced by standards.

In whole blood samples, hematocrit or percentage of red blood cells by volume in the whole blood sample is a variable and can be taken into account when analyzing ghrelin levels that are present in the plasma component. As the hematocrit of a patient's blood rises, so does the volume of plasma in a fixed volume sample, which is introduced into the test device decreases and vice versa. Since it is the plasma component which exclusively carries the ghrelin levels being measured, then the lower the volume of plasma component added to the reaction mix, the lower the resulting concentration of the substance being measured in that reaction mix and the resulting assayed value and vice versa.

Any analysis that produces a concentration of a plasma substance in whole blood may be corrected for variations in hematocrit to give a true plasma concentration. It can be most useful in these situations to measure two substances, one of which is ghrelin under investigation and the other which is considered to be a marker by which to estimate or normalize the sample hematocrit. The hemoglobin concentration of whole blood, after red blood cells are lysed, is directly proportional to the red blood cell volume in the whole blood sample.

Pharmaceutical Compositions

Ghrelin described herein can be formulated as a pharmaceutical composition, e.g., flash frozen or lyophilized for storage and/or transport. In some embodiments, the compound can be in a composition with sterile saline, for example. In some embodiments, a ghrelin can be reconstituted in such saline or other acceptable diluent. In some embodiments, about 10 μg ghrelin powder is reconstituted in about 100 μL saline solution before administration. In addition, the composition can be administered alone or in combination with a carrier, such as a pharmaceutically acceptable carrier or a biocompatible scaffold. Compositions of the invention may be conventionally administered parenterally, by injection, for example, intravenously, subcutaneously, or intramuscularly. Additional formulations which are suitable for other modes of administration include oral formulations. Oral formulations include such normally employed excipients such as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, about 25% to about 70%.

Typically, compositions are administered in a manner compatible with the dosage formulation, and in such amount as will be therapeutically effective for the disease or condition by treated. The quantity to be administered depends on the subject to be treated. Precise amounts of the composition to be administered depend on the judgment of the practitioner. Suitable regimes for initial administration and boosters are also variable, but are typified by an initial administration followed by subsequent administrations.

In some embodiments, additional pharmaceutical compositions are administered to a subject to support or augment the compositions as described herein. Different aspects of the present invention involve administering an effective amount of the composition to a subject. Additionally, such compositions can be administered in combination with other agents. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

Suitable pharmaceutical carriers include inert solid diluents or fillers, sterile aqueous solution and various organic solvents. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Nasal aerosol or inhalation formulations may be prepared, for example, as solutions in saline, employing benzyl alcohol or other suitable preservatives, absorption promoters to enhance bioavailability, employing fluorocarbons, and/or employing other solubilizing or dispersing agents.

An effective amount of therapeutic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

Ghrelin compositions can be produced using techniques well known in the art. For example, a polypeptide region of ghrelin can be chemically or biochemical synthesized and modified. Techniques for chemical synthesis of polypeptides are well known in the art (Lee V. H. L. in "Peptide and Protein Drug Delivery", New York, N.Y., M. Dekker, 1990). Examples of techniques for biochemical synthesis involving the introduction of a nucleic acid into a cell and expression of nucleic acids are provided in Ausubel F. M. et al., "Current Protocols in Molecular Biology", John Wiley, 1987-1998, and Sambrook J. et al., "Molecular Cloning, A Laboratory Manual", 2d Edition, Cold Spring Harbor Laboratory Press, 1989, each of which is incorporated herein by reference. Another exemplary technique described in U.S. Pat. No. 5,304,489, incorporated herein by reference, is the use of a transgenic mammal having mammary gland-targeted mutations, which result in the production and secretion of synthesized ghrelin in the milk of the transgenic mammal.

Ghrelin can also be produced recombinantly using routine expression methods known in the art. The polynucleotide encoding the desired ghrelin (e.g., primarily sequence of ghrelin as given in SEQ ID NO. 1) is operably linked to a promoter into an expression vector suitable for any convenient host. Both eukaryotic and prokaryotic host systems are used in forming recombinant ghrelin. Ghrelin is then isolated from lysed cells or from the culture medium and purified to the extent needed for its intended use. Isolated ghrelin may be modified or further modified at serine amino acid position 2 and/or serine amino acid position 3 by fatty acid acylation in vivo or in vitro, with the latter in vitro acylation reaction condition comprising fatty acid thioester, ghrelin, and microsomes comprising ghrelin O-acyl transferase (GOAT). In some embodiments, acyl ghrelin modified with fatty acid at serine amino acid position 2 and/or serine amino acid position 3 is isolated from cellular or reaction components.

Ghrelin compositions can include pharmaceutically acceptable salts of the compounds therein. These salts will be ones which are acceptable in their application to a pharmaceutical use, meaning that the salt will retain the biological activity of the parent compound and the salt will not have untoward or deleterious effects in its application and use in treating diseases. Pharmaceutically acceptable salts are prepared in a standard manner.

Ghrelin compositions may be administered in the form of an alkali metal or earth alkali metal salt thereof, concurrently, simultaneously, or together with a pharmaceutically acceptable carrier or diluent, especially and in the form of a pharmaceutical composition thereof, whether by various routes (e.g., oral, rectal, parenteral, subcutaneous) in an effective amount.

Administration of Compositions

The present disclosure provides for a method of reducing the incidence or severity of mBI in a subject, comprising administering to the subject an effective amount of a compound comprising ghrelin, thereby reducing the incidence or severity of the mBI. The present disclosure also provides for methods of reducing the incidence or severity of mBI in a subject, comprising administering to the subject an effective amount of ghrelin, thereby reducing the incidence or severity of the mBI. This invention further provides for methods of reducing the amount of time needed to recover from a mild brain injury, comprising administering to a patient suffering from a mild brain injury a therapeutically effective amount of ghrelin within a certain period (e.g., 72 hours) of the mild brain injury.

In some embodiments, ghrelin is administered prior to an event or activity with a potential for occurrence of mBI. In some embodiments, the event or activity is participation in a sporting event, physical training, or combat. In some embodiments, the event or activity is baseball, basketball, rugby, football, hockey, lacrosse, soccer, cycling, boxing, gymnastics, a martial art, a mixed martial art, a military exercise, automobile racing, snow skiing, snowboarding, ice skating, skateboarding, motocross, mountain biking, motorcycle and ATV riding, and the like. In some embodiments, the subject has not suffered a mBI. In some embodiments, the subject has a history of mBI or is susceptible to mBI.

In some embodiments, an administration route for a ghrelin is selected from: buccal delivery, sublingual delivery, transdermal delivery, inhalation and needle-free injection, such as using the methods developed by PowderJet. For inhalation, ghrelin can be formulated using methods known to those skilled in the art, for example an aerosol, dry powder or solubilized such as in microdroplets, in a device intended for such delivery (such as commercially available devices and formulation technologies from Aradigm Corp. (Hayward, Calif.), Alkermes, Inc. (Cambridge, Mass.), Nektar Therapeutics (San Carlos, Calif.), Windgap Medical, Inc. (e.g., Abiliject™) or MannKind Corporation (Valencia, Calif.; e.g., Technosphere®, Dreamboat®, and Cricket™ technologies)).

In some embodiments, the ghrelin is administered via a powder or stable formulation, wherein ghrelin is formulated in a dosage form selected from the group consisting of: liquid, beverage, medicated sports drink, powder, capsule, chewable tablet, caplet, swallowable tablet, buccal tablet, troche, lozenge, soft chew, solution, suspension, spray, suppository, tincture, decoction, infusion, and a combination thereof.

In some embodiments, ghrelin is administered via inhalation, oral, intravenous, parenteral, buccal, subcutaneous, transdermal, patch, sublingual, intramuscular, or intranasal. In some embodiments, ghrelin is administered in a single dose. In some embodiments, ghrelin is administered in multi-doses. In some embodiments, ghrelin is administered at a dosage from 10 ng/kg per day to 10 mg/kg per day (or any sub value or sub range there between, e.g., 0.1 µg/kg per day to 5 mg/kg per day). In some embodiments, a dosing regimen (2 µg/kg, for example delivered intravenously) is administered within 8 hours following injury. The dosing is a one-time dose with possible recurrent dosing based on patient symptoms.

Nasal delivery is a non-invasive route for therapeutics targeting the central nervous system because of relatively high permeability of nasal epithelium membrane, avoidance of hepatic first pass elimination. Nasal delivery is easy to administer and allows for self-medication by an individual. Nasal mucociliary clearance is an important limiting factor to nasal drug delivery. Nasal mucociliary clearance severely limits the time allowed for drug absorption to occur and may effectively prevent sustained drug administration. However, it has been documented that nasal administration of certain hormones has resulted in a more complete administration. In some embodiments, the present disclosure utilizes nasal delivery of ghrelin.

In some embodiments, a composition comprising ghrelin that is suitable for nasal administration may include one or more bioadhesive polymers. Some polymers such as carbopol, can adhere onto the nasal mucosa for reasonably prolonged periods, preventing rapid nasal clearance. In some embodiments, a composition suitable for nasal administration, the percentage of bioadhesive polymer in a suitable solution of ghrelin is about 0.1%. In some embodiments, a composition suitable for nasal administration, the percentage of bioadhesive polymer in a suitable solution of ghrelin is about 0.5%. In some embodiments, a composition suitable for nasal administration, the percentage of bioadhesive polymer in a suitable solution of ghrelin is about 1%. In some embodiments, a composition suitable for nasal administration, the percentage of bioadhesive polymer in a suitable solution of ghrelin is about 5%.

In some embodiments, a composition comprising ghrelin that is suitable for nasal administration may include one or more surfactants. Surfactants that may be used in the compositions of the present invention include different polyethylene glycols (PEGS) and polyethylene glycol-derivatives. In some embodiments, a composition suitable for nasal administration, the percentage of surfactant in a suitable solution of ghrelin is about 1%. In some embodiments, a composition suitable for nasal administration, the percentage of surfactant in a suitable solution of ghrelin is about 2%. In some embodiments, a composition suitable for nasal administration, the percentage of surfactant in a suitable solution of ghrelin is about 5%. In some embodiments, a composition suitable for nasal administration, the percentage of surfactant in a suitable solution of ghrelin is about 10%.

In some embodiments, a composition comprising ghrelin that is suitable for nasal administration may include one or more buffering agents for controlling the pH of the composition. Buffering agents that may be used in the compositions of the present invention include citric acid and sodium citrate dihydrate. In some embodiments, a composition suitable for nasal administration, the percentage of buffering agent in a suitable solution of ghrelin is about 0.001%. In some embodiments, a composition suitable for nasal administration, the percentage of buffering agent in a suitable solution of ghrelin is about 0.005%. In some embodiments, a composition suitable for nasal administration, the percentage of buffering agent in a suitable solution of ghrelin is about 0.01%. In some embodiments, a composition suitable for nasal administration, the percentage of buffering agent in a suitable solution of ghrelin is about 0.1%.

In some embodiments, the osmolarity of the composition comprising ghrelin may be controlled by propylene glycol. When a composition comprising ghrelin is a gel, the composition may include a gelling agent such as hydroxylpropyl cellulose, carbopols, carboxymethylcellulose, and ethylcellulose. In some embodiments, the composition comprising ghrelin may include a preservative such as ethylenediaminetetraacetic acid (EDTA) and benzalkonium chloride. Non-limiting examples of suitable solvents for compositions of the present invention include water, vegetable oil and ethanol. In some embodiments, the use of a nasal inhalant reduces the concentration required to treat mBI and prevent unwanted side effects.

In some embodiments, nasal administration is a more practical means of delivery in a military or sport setting. In some embodiments, the present invention provides a method for improving the standard of care for preventing or treating mBI in military personnel or athletes through a prophylactic and post-acute intranasal therapeutic. In some embodiments, the active ingredient of the therapeutic is ghrelin. In some embodiments, ghrelin may be part of a formulation that is delivered intranasally to facilitate ease of access and use in the field and to minimize the dose required further limiting side effects. Using ghrelin as a therapeutic may reduce poor outcomes following injury, especially neuropsychological and neurodegenerative disorders including Chronic Traumatic Encephalopathy (CTE) and Post-Traumatic Stress Disorder (PTSD) linked to repetitive brain injuries, an increasing concern for today's military personnel and athletes.

In some embodiments, the present invention provides compositions comprising ghrelin that are applied as nasal drops, eye drops and nasal sprays. For the nasal application, a solution or suspension may be used which is applied as spray, i.e., in the form of a fine dispersion in air or by means of a conventional spray-squeeze bottle or pump. Suitable nontoxic pharmaceutically acceptable carriers for use in a drug delivery system for intranasal administration of ghrelin may include, but not limited to, carriers used for nasal pharmaceutical formulations for other steroids, such as estrogen.

In some embodiments, formulations of the present invention may contain a preservative and/or stabilizer. These include, but not limited to, ethylene diamine tetraacetic acid (EDTA) and its alkali salts (for example dialkali salts such as disodium salt, calcium salt, calcium-sodium salt), lower alkyl p-hydroxybenzoates, chlorhexidine (for example in the form of the acetate or gluconate) and phenyl mercury borate. Other suitable preservatives are: pharmaceutically useful quaternary ammonium compounds, for example cetylpyridinium chloride, tetradecyltrimethyl ammonium bromide, generally known as "cetrimide", N-Benzyl-N,N-dimethyl-2-{2-[4-(2,4,4-trimethylpentan-2-yl)phenoxy] ethoxy}ethanaminium chloride, generally known as "benzethonium chloride" and myristyl picolinium chloride. Each of these compounds may be used in a concentration of about 0.002 to 0.05%, for example about 0.02% (weight/volume in liquid formulations, otherwise weight/weight). In some embodiments, preservatives among the quaternary ammonium compounds are, but not limited to, alkylbenzyl dimethyl ammonium chloride and mixtures thereof, for example, benzalkonium chloride.

In some embodiments, the present invention provides for a treatment strategy for athletes who have suffered a mBI that may not only reduce the time required for safe return to play but also provide protection from future mBI.

Intranasal (IN) administrations may have fewer side effects than intraperitoneal (IP) administrations due to a shift in pharmaceutical research to nasal sprays, drops and gels: the nasal route of drug administration continues to receive increasing attention from pharmaceutical scientists and clinicians because this route circumvents hepatic first pass elimination associated with oral delivery, is easily accessible and suitable for self-medication. Intranasal administration also particularly suits drugs targeting the brain because certain drug solutions can bypass the blood-brain barrier (BBB) and reach the central nervous system (CNS) directly from the nasal cavity—uptake of these drugs depends on their molecular weight and lipophilicity. The intranasal delivery increases brain levels of the drug while decreasing systemic concentrations and thus should have less harmful side effects.

In some embodiments, the present invention provides a method of prophylactically administering a composition comprising ghrelin to individuals who are involved in activities, such as contact sports or serving in the armed forces, where there is a possibility of the individuals suffering mBI. In some embodiments, the present invention provides a method for acutely treating individuals who have suffered mBI. For acute treatments, nasal administration of the composition comprising ghrelin may reduce the time for uptake and increase the concentration of ghrelin that reaches the blood or brain.

For oral administration, such excipients include, e.g., pharmaceutical grades of mannitol, lactose, starch, magnesium stearate, sodium saccharine, talcum, cellulose, glucose, gelatin, sucrose, magnesium carbonate, and the like. In powders, the carrier is a finely divided solid, which is a mixture with the finely divided active component. In tablets, the active component is mixed with the carrier having the necessary binding capacity in suitable proportions and compacted in the shape and size desired. The powders and tablets contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include a composition comprising an active compound disclosed herein with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Other forms suitable for oral administration include liquid form preparations including emulsions, syrups, elixirs, aqueous solutions, aqueous suspensions, toothpaste, gel dentifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The administration of ghrelin is based on suitable dosing regimens that take into account factors well-known in the art including, e.g., type of subject being dosed; age, weight, sex and medical condition of the subject; the route of administration; the renal and hepatic function of the subject; the desired effect; and the particular compound employed. Optimal precision in achieving concentrations of drug within the range that yields efficacy without toxicity requires a regimen based on the kinetics of the drug's availability to target sites. This involves a consideration of the distribution, equilibrium, and elimination of a drug.

In some embodiments, ghrelin composition is administered subcutaneously. In some embodiments, ghrelin composition is administered as a bolus, wherein the administration form may be any suitable parenteral form.

Pharmaceutical compositions for parenteral administration include sterile aqueous and non-aqueous injectable solutions, dispersions, suspensions or emulsions, as well as sterile powders to be reconstituted in sterile injectable solutions or dispersions prior to use. Other suitable administration forms include suppositories, sprays, ointments, creams, gels, inhalants, dermal patches, implants, pills, tablets, lozenges and capsules.

A typical non-limiting dosage is in a concentration equivalent to from 10 ng to 10 mg ghrelin per kg bodyweight. In some embodiments, ghrelin is administered in a concentration equivalent to from about 0.1 µg to about 1 mg ghrelin per kg bodyweight, such as from about 0.5 µg to about 0.5 mg ghrelin per kg bodyweight, such as from about 1.0 µg to about 0.1 mg ghrelin per kg bodyweight, such as from about 1.0 µg to about 50 µg ghrelin per kg bodyweight, such as from about 1.0 µg to about 10 µg ghrelin per kg bodyweight.

In some embodiments, an intravenous injection of ghrelin is employed. The administration route must ensure that the non-degraded, bioactive form of the peptide will be the dominating form in the circulation, which will reach and stimulate the ghrelin receptors in order to obtain the maximum effect of ghrelin treatment on mBI. In some embodiments, ghrelin is administered within about 30 minutes of the incident that results in mBI. In some embodiments, the ghrelin is administered within about 30 minutes to about 2 hours of the incident that results in mBI. In some embodiments, ghrelin is administered within about 30 minutes to about 6 hours of the incident that results in mBI. In some embodiments, ghrelin is administered within about 30 minutes to about 12 hours of the incident that results in mBI.

Ghrelin compositions may be formulated for parenteral administration (e.g., by injection, for example bolus injection or continuous infusion) and may be presented in unit dose form in ampules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Alternatively, the active ingredient may be in powder form, obtained by aseptic isolation of sterile solid or by lyophilization from solution for constitution before use with a suitable vehicle, e.g., sterile, pyrogen-free water. Aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

The pharmaceutical dosage forms suitable for injection or infusion can include sterile aqueous solutions or dispersions comprising the active ingredient that are adapted for administration by encapsulation in liposomes. In all cases, the ultimate dosage form must be sterile, fluid and stable under the conditions of manufacture and storage. Sterile injectable solutions are prepared by incorporating ghrelin or pharmaceutical acceptable salt thereof in the required amount in the appropriate solvent with various of the other ingredients enumerated above, as required, followed by, e.g., filter sterilization.

Ghrelin compounds can also be delivered topically. Regions for topical administration include the skin surface and also mucous membrane tissues of the rectum, nose, mouth, and throat. Compositions for topical administration via the skin and mucous membranes should not give rise to signs of irritation, such as swelling or redness.

Ghrelin compounds may include a pharmaceutical acceptable carrier adapted for topical administration. Thus, the composition may take the form of, for example, a suspension, solution, ointment, lotion, cream, foam, aerosol, spray, suppository, implant, inhalant, tablet, capsule, dry powder, syrup, balm or lozenge. Methods for preparing such compositions are well known in the pharmaceutical industry.

Ghrelin compounds may be administered transdermally, which involves the delivery of a pharmaceutical agent for percutaneous passage of the drug into the systemic circulation of the patient. The skin sites include anatomic regions for transdermally administering the drug and include the forearm, abdomen, chest, back, buttock, and the like. Transdermal delivery is accomplished by exposing a source of the active compound to a patient's skin for an extended period of time. Transdermal patches can add advantage of providing controlled delivery of a compound complex to the body. Such dosage forms can be made by dissolving, dispersing, or otherwise incorporating ghrelin compound in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Kits

Ghrelin compositions may be administered alone or in combination with pharmaceutically acceptable carriers or excipients, in either single or multiple doses. The formulations may conveniently be presented in unit dosage form by methods known to those skilled in the art. The compounds can be provided in a kit. Such a kit typically contains an active compound in dosage forms for administration. The kit comprises an amount of dosage units corresponding to the relevant dosage regimen. In some embodiment, the kit comprises a pharmaceutical composition comprising a ghrelin compound or a pharmaceutically acceptable salt thereof and pharmaceutically acceptable carrier, vehicles and/or excipients, said kit having multiple dosage units. The dosage units comprise an amount of ghrelin or a salt thereof equivalent to from about 0.3 µg to about 600 mg ghrelin, such as from about 2.0 µg to about 200 mg ghrelin, such as from about 5.0 µg to about 100 mg ghrelin, such as from about 10 µg to about 50 mg ghrelin, such as from about 10 µg to about 5 mg ghrelin, such as from about 10 µg to about 1.0 mg ghrelin.

The kit contains instructions indicating the use of the dosage form to achieve a desirable affect and the amount of dosage form to be taken over a specified time period. Accordingly, in one embodiment the kit comprises instructions for administering the pharmaceutical composition. In particular said instructions may include instructions referring to administration of said pharmaceutical composition after mBI or concussion, or at the most about 12 hours after the incident causing mBI or concussion, such as at the most about 6 hours after the incident causing mBI or concussion, such as at the most about 3 hours after the incident causing mBI or concussion, such as at the most about 1 hours after the incident causing mBI or concussion, such as at the most about 30 minutes after the incident causing mBI or concussion, such as at the most about 10 minutes after the incident causing mBI or concussion, such as at the most about 5 minutes after the incident causing mBI or concussion.

EXAMPLES

The following Examples are intended to further illustrate certain embodiments of the disclosure and are not intended to limit its scope.

Example 1

Ghrelin administration reduces oxidative burst in inflammatory cells following mBI. Since no well-accepted animal model exists for concussions, a very small cerebral lesion that closely mimics mBI is used as a model of mBI. C57/B6 mice anesthetized with 5% isoflurane in oxygen (1.7 L/min) are given 0.3 mg/kg buprenorphine subcutaneously for analgesia prior to infliction of the mild brain injury. Anesthesia is assessed by paw pinch reflex. After creating a burr hole through the dura with a dental drill, a lesion using a controlled cortical impactor (CCI) is used to create injury 1 mm lateral and posterior to the bregma (5.0 mm/sec at a depth of 1.0 mm).

Animals are separated into three treatment groups: 1) Sham, 2) mBI, and 3) mBI plus ghrelin. A variety of doses can be tested depending upon the particular ghrelin. Ghrelin can be obtained for example from Phoenix Pharmaceuticals, Inc. (Burlingame, Calif.). For example, 1 to 50 µg at one or more time points. As one example, treatment with subcutaneous ghrelin: 1 dose of 10 µg following mBI and additional dose 10 µg 1 hour after. Brain tissue is harvested at 2-8 hours, preferably about 6 hours post-injury. Reactive oxygen species (ROS) is measured by neutrophil oxidative burst in leukocytes isolated from brain tissue as shown in FIG. 1, which depicts the principle of assaying oxidative burst within inflammatory cells. Dihydrorhodamine 123 (DHR 123) diffuses across the cell membrane. When it encounters reactive oxygen species (ROS), DHR 123 is oxidized and fluoresces green. The fluorescence is then measured and presented as arbitrary fluorescence unit (AFU), wherein higher intensity means greater oxidative burst and, therefore greater concentration or amount of ROS. Brain cells are isolated (for example by collagenase Dispase/DNAse and a Percoll gradient with resuspension of the pellet using 100 μL of HBSS). Oxidative burst, which is a marker for ROS, can be measured by flow cytometry (e.g., FL1 channel with 488-nm laser).

Figure 2:
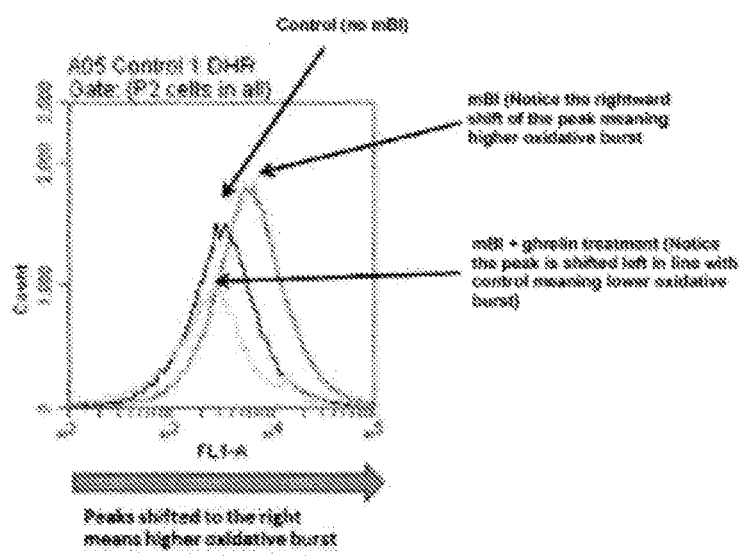
FIG. 2 depicts subcutaneous administration of ghrelin resulting in reduced oxidative burst in inflammatory cells following mBI. Rightward shift in peak reflects higher oxidative burst. Higher oxidative burst is observed in mBI alone, and lower oxidative burst is observed in ghrelin treated mBI. For the ghrelin treatment, the peak is shifted left in line with control meaning lower oxidative burst.
Figure 3:
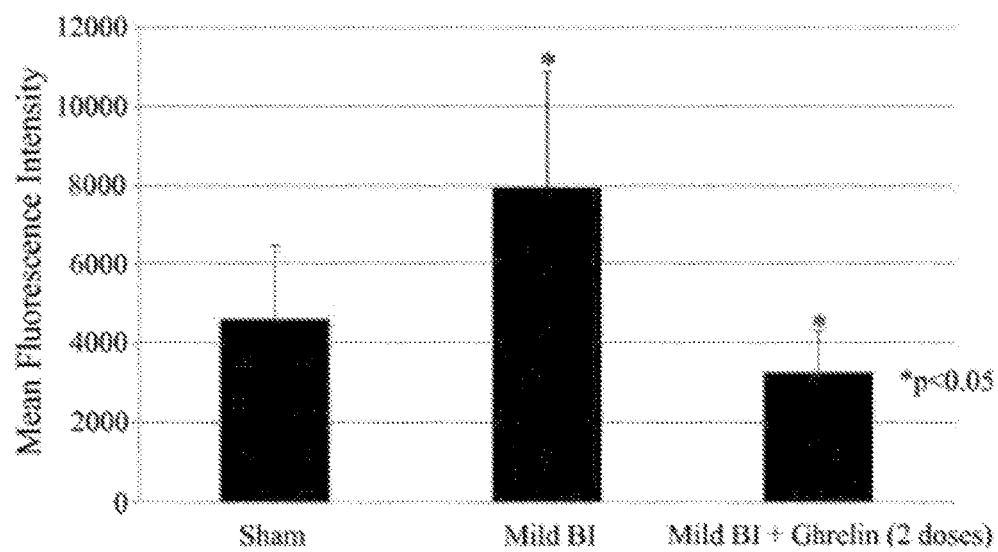
FIG. 3 depicts oxidative burst of ipsilateral whole brain following mild BI. Mild BI plus ghrelin reduces oxidative burst as quantified by arbitrary fluorescence unit (AFU). Oxidative burst is increased in animals following mBI compared to sham control (7963 AFU±2900 (mild BI) vs. 4624 AFU±1858 (sham); n=5 animals in each group). Ghrelin treatment reduces the oxidative burst compared to mBI (7963 AFU±2900 (mild BI) vs. 3257 AFU±1031 (mild BI+ghrelin (2 doses)); p-value of 0.048 using Student's t-test). AFU equals mean fluorescence intensity.

Oxidative burst is increased in animals following mBI compared to control. The number of animals was three in each group (n=3 animals in each group). Ghrelin treatment reduced the oxidative burst compared to untreated animal with mBI (FIG. 2). FIG. 2 shows that subcutaneous ghrelin reduces oxidative burst in inflammatory cells following mBI. The impact on mBI when ghrelin is administered can be quantified, for example, by arbitrary fluorescence unit (AFU) (FIG. 3). FIG. 3 depicts quantitation of oxidative burst of ipsilateral whole brain following mild BI. Oxidative burst increased in animals following mBI compared to control. Ghrelin treatment reduced the oxidative burst compared to untreated mBI (FIG. 2 and FIG. 3).

As quantified in FIG. 3, oxidative burst was increased in animals following mBI compared to sham control (7963 AFU±2900 (mild BI) vs. 4624 AFU±1858 (sham); n=5 animals in each group). Ghrelin treatment reduced the oxidative burst compared to mBI (7963 AFU±2900 (mild BI) vs. 3257 AFU±1031 (mild BI+ghrelin (2 doses)); p-value of 0.048 using Student's t-test).

Example 2

The binding ability of ghrelin to GHS-R can be determined by a binding assay. Chinese hamster ovary cell line cells, CHO-K1, are prepared to express the human recombinant GHS receptor.

The cells can be prepared by any suitable method. One such method can include: The cDNA for human growth hormone secretagogue receptor (hGHS-R1a, or ghrelin receptor) is cloned by Polymerase Chain Reaction (PCR) using human brain RNA as a template (Clontech, Palo Alto, Calif.), gene specific primers flanking the full-length coding sequence of hGHS-R, (S: 5'-ATGTGGAACGCGACGC-CCAGCGAAGAG-3' (SEQ ID NO: 2) and AS: 5'-TCAT-GTATTAATACTAGATTCTGTCCA-3') (SEQ ID NO: 3), and Advantage 2 PCR Kit (Clontech). The PCR product is cloned into the pCR2.1 vector using Original TA Cloning Kit (Invitrogen, Carlsbad, Calif.). The full length human GHS-R is subcloned into the mammalian expression vector pcDNA 3.1 (Invitrogen). The plasmid is transfected into the Chinese hamster ovary cell line, CHO-K1 (American Type Culture Collection, Rockville, Md.), by calcium phosphate method (Wigler, M et al., Cell 11, 223, 1977). Single cell clones stably expressing the hGHS-R are obtained by selecting transfected cells grown in cloning rings in RPMI 1640 media supplemented with 10% fetal bovine serum and 1 mM sodium pyruvate containing 0.8 mg/ml G418 (Gibco, Grand Island, N.Y.).

GHS-R binding assay is performed by homogenizing the CHO-K1 cells expressing the human recombinant GHS receptor in 20 ml of ice-cold 50 mM Tris-HCl with a Brinkman Polytron (Westbury, N.Y.). The homogenates are washed twice by centrifugation (39,000 g/10 min), and the final pellets are resuspended in 50 mM Tris-HCl, containing 2.5 mM $MgCl_2$, and 0.1% BSA. For the GHS-R binding assay, aliquots (0.4 ml) are incubated with 0.05 nM ($^{125}$I) ghrelin (~2000 Ci/mmol, Perkin Elmer Life Sciences, Boston, Mass.), with and without 0.05 ml of unlabeled competing test peptides. After a 60 min incubation (4° C.), the bound ($^{125}$I) ghrelin is separated from the free by rapid filtration through GF/C filters (Brandel, Gaithersburg, Md.), which have been previously soaked in 0.5% polyethyleneimine/0.1% BSA. The filters then are washed three times with 5 ml aliquots of 50 mM Tris-HCl and 0.1% bovine serum albumin, and the bound radioactivity trapped on the filters is counted by gamma spectrometry (Wallac LKB, Gaithersburg, Md.). Specific binding is defined as the total ($^{125}$I) ghrelin bound minus that bound in the presence of 1000 nM ghrelin.

Example 3

The functional activity of ghrelin is examined using GHS-R functional activity assays in vitro and in vivo. Ghrelin binding to GSH receptor can mediate intracellular i$Ca^{2+}$ mobilization in vitro. Ghrelin may also be tested for ability to stimulate or suppress release of growth hormone (GH) in vivo.

Cells expressing human GSH receptor can be used. For example, CHO-K1 cells expressing the human GSH receptor are harvested by incubating in a 0.3% EDTA/phosphate buffered saline solution (25° C.), and are washed twice by centrifugation. The washed cells are resuspended in Hank's—buffered saline solution (HBSS) for loading of the fluorescent $Ca^{2+}$ indicator Fura-2AM. Cell suspensions of approximately $10^6$ cells/ml are incubated with 2 μM Fura-2AM for 30 min at about 25° C. Unloaded Fura-2AM is removed by centrifugation twice in HBBS, and the final suspensions are transferred to a spectrofluorometer (Hitachi F-2000) equipped with a magnetic stirring mechanism and a temperature-regulated cuvette holder. After equilibration to 37° C., ghrelin is added for measurement of intracellular $Ca^{2+}$ mobilization. The excitation and emission wavelengths can be, for example, 340 and 510 nm, respectively.

Ghrelin may be tested for its ability to stimulate or suppress release of growth hormone (GH) in vivo (Deghenghi, R., et al., *Life Sciences,* 1994, 54, 1321-1328; International Application No. WO 02/08250; each of which is incorporated herein by reference in its entirety). Thus, for example, in order to ascertain ghrelin's ability to stimulate GH release in vivo the compound may be injected subcutaneously in 10-day old rats at a dose of, e.g., 300 mg/kg. The circulating GH may be determined at, e.g., 15 minutes after injection and compared to GH levels in rats injected with a solvent control.

It is to be understood that while the present disclosure has been described in conjunction with the above embodiments, that the foregoing description and examples are intended to illustrate and not limit the scope of the present disclosure. Other aspects, advantages and modifications within the scope of the present disclosure will be apparent to those skilled in the art to which the present disclosure pertains.

The present disclosure is not to be limited in scope by the specific embodiments described which are intended as single illustrations of individual aspects of the present disclosure, and any compositions or methods, which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. A method of treating mild traumatic brain injury (mTBI) in a subject, comprising administering to the subject a therapeutically effective amount of ghrelin, thereby treating the mTBI, wherein a selective androgen receptor modulator is not administered.

2. The method of 1, wherein the ghrelin has the sequence of Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg (SEQ ID NO. 1).

3. The method of claim 2, wherein the ghrelin is modified with one or more fatty acids.

4. The method of claim 3, wherein the fatty acid is an octanoic acid.

5. The method of claim 2, wherein the ghrelin is modified at serine at amino acid position 2 and/or serine at amino acid position 3 of SEQ ID NO. 1.

6. The method of claim 5, wherein the ghrelin is modified at serine at amino acid position 2 and/or serine amino acid position 3 with an octanoic acid.

7. The method of claim 6, wherein modification of ghrelin is acylation of ghrelin at serine at amino acid position 2 and/or serine at amino acid position 3 with an octanoic acid.

8. The method of claim 1, wherein the subject is a mammal.

9. The method of claim 1, wherein ghrelin is administered within not more than about 24 hours of the mTBI.

10. The method of claim 9, wherein ghrelin is administered within not more than about 8 hours of the mTBI.

11. The method of claim 1, wherein the ghrelin is administered in an amount that results in ghrelin blood levels being at least two times greater than the endogenous ghrelin blood levels of the subject.

12. The method of claim 1, wherein ghrelin is administered in a single dose.

13. The method of claim 1, wherein ghrelin is administered at a dosage from 10 ng/kg per day to 10 mg/kg per day.

14. The method of claim 13, wherein ghrelin is administered at a dosage of 2 µg/kg per day.

15. A method of treating mild traumatic brain injury (mTBI) in a subject, comprising administering to the subject a therapeutically effective amount of ghrelin in an amount that provides blood levels of ghrelin that are at least 1.5 times greater than endogenous ghrelin blood levels of the subject, thereby treating the mTBI.

16. The method of claim 15, wherein the ghrelin has the sequence of Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg (SEQ ID NO. 1).

17. The method of claim 15, wherein the ghrelin is modified with one or more fatty acids.

18. The method of claim 17, wherein the fatty acid is an octanoic acid.

19. The method of claim 16, wherein the ghrelin is modified at serine at amino acid position 2 and/or serine at amino acid position 3 of SEQ ID NO. 1.

20. The method of claim 19, wherein the ghrelin is modified at serine at amino acid position 2 and/or serine at amino acid position 3 with an octanoic acid.

21. The method of claim 20, wherein modification of ghrelin is acylation of ghrelin at serine at amino acid position 2 and/or serine at amino acid position 3 with an octanoic acid.

22. The method of claim 15, wherein ghrelin is administered in a single dose.

23. The method of claim 15, wherein the amount administered provides a blood level of at least 1.5 to 100 times greater the amount found endogenously in the subject.

24. The method of claim 23, wherein the amount administered results in a blood level of at least 55 picograms/mL.

25. The method of claim 23, wherein ghrelin is administered at a dosage from 10 ng/kg per day to 10 mg/kg per day.

* * * * *